US010815235B2

(12) United States Patent
Armer et al.

(10) Patent No.: US 10,815,235 B2
(45) Date of Patent: *Oct. 27, 2020

(54) POLYCYCLIC COMPOUNDS AND USES THEREOF

(71) Applicant: XOC Pharmaceuticals, Inc., Los Gatos, CA (US)

(72) Inventors: Thomas Armer, Los Gatos, CA (US); Scott Borland, Los Gatos, CA (US); Miguel Guzman, Los Gatos, CA (US)

(73) Assignee: Xoc Pharmaceuticals, Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,713

(22) Filed: Apr. 10, 2019

(65) Prior Publication Data

US 2019/0233419 A1 Aug. 1, 2019

Related U.S. Application Data

(63) Continuation of application No. 15/997,616, filed on Jun. 4, 2018, which is a continuation of application No. PCT/US2018/035701, filed on Jun. 1, 2018.

(60) Provisional application No. 62/513,998, filed on Jun. 1, 2017.

(51) Int. Cl.
*A61K 31/48* (2006.01)
*C07D 471/06* (2006.01)
*C07D 457/12* (2006.01)
*A61P 25/16* (2006.01)
*A61P 25/06* (2006.01)
*A61P 7/06* (2006.01)
*A61P 7/04* (2006.01)
*A61P 25/28* (2006.01)
*A61P 9/00* (2006.01)

(52) U.S. Cl.
CPC .............. *C07D 471/06* (2013.01); *A61P 7/04* (2018.01); *A61P 7/06* (2018.01); *A61P 9/00* (2018.01); *A61P 25/06* (2018.01); *A61P 25/16* (2018.01); *A61P 25/28* (2018.01); *C07D 457/12* (2013.01)

(58) Field of Classification Search
CPC .................................. A61K 31/48; A61P 9/00
USPC ........................................................ 514/288
See application file for complete search history.

(56) References Cited

U.S. PATENT DOCUMENTS

| | | |
|---|---|---|
| 705,519 A | 7/1902 | Eiseman |
| 2,086,559 A | 7/1937 | Kharasch |
| 3,085,092 A | 4/1963 | Hoffman et al. |
| 3,536,809 A | 10/1970 | Applezweig |
| 3,598,123 A | 8/1971 | Zaffaroni et al. |
| 3,710,795 A | 1/1973 | Higuchi et al. |
| 3,822,268 A | 7/1974 | Mago et al. |
| 3,845,770 A | 11/1974 | Theeuwes et al. |
| 3,916,899 A | 11/1975 | Theeuwes et al. |
| 3,922,347 A | 11/1975 | Bach et al. |
| RE28,819 E | 5/1976 | Thompson |
| 4,005,089 A | 1/1977 | Mago Nee Karacsony et al. |
| 4,008,719 A | 2/1977 | Theeuwes et al. |
| 4,044,126 A | 8/1977 | Cook et al. |
| 4,165,376 A | 8/1979 | Rosenberg |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,515,950 A | 5/1985 | Brich et al. |
| 4,522,811 A | 6/1985 | Eppstein et al. |
| 4,675,404 A | 6/1987 | Bernardi et al. |
| 4,692,452 A | 9/1987 | Cerny et al. |
| 4,748,248 A | 5/1988 | Sauer et al. |
| 4,828,950 A | 5/1989 | Crandall |
| 4,874,768 A | 10/1989 | Huth et al. |
| 4,950,672 A | 8/1990 | Haefliger |
| 4,970,314 A | 11/1990 | Borner et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,212,178 A | 5/1993 | Sauer et al. |
| 5,323,907 A | 6/1994 | Kalvelage |
| 5,354,556 A | 10/1994 | Sparks et al. |
| 5,401,748 A | 3/1995 | Sauer et al. |
| 5,411,966 A | 5/1995 | Sauer et al. |
| 5,547,958 A | 8/1996 | Sauer et al. |

(Continued)

FOREIGN PATENT DOCUMENTS

| | | |
|---|---|---|
| AU | 2506788 A | 3/1989 |
| AU | 618290 B2 | 12/1991 |

(Continued)

OTHER PUBLICATIONS

Dumitrascu et al. Terguride ameliorates monocrotaline-induced pulmonary hypertension in rats. Eur Respir J 37:1104-1118 (2011).

(Continued)

*Primary Examiner* — Charanjit Aulakh

(74) *Attorney, Agent, or Firm* — Wilson Sonsini Goodrich & Rosati

(57) ABSTRACT

The present invention provides novel neuromodulatory compounds and compositions thereof. The invention also relates to methods of treating various diseases, disorders, and conditions using the compounds of this invention; processes for preparing the compounds of this invention; as well as intermediates for the preparation compounds.

17 Claims, No Drawings

(56) References Cited

U.S. PATENT DOCUMENTS

| | | |
|---|---|---|
| 5,591,767 A | 1/1997 | Mohr et al. |
| 5,639,476 A | 6/1997 | Oshlack et al. |
| 5,639,480 A | 6/1997 | Bodmer et al. |
| 5,668,155 A | 9/1997 | Cincotta et al. |
| 5,674,533 A | 10/1997 | Santus et al. |
| 5,705,519 A | 1/1998 | Audia et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,877,183 A | 3/1999 | Cincotta |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,037,346 A | 3/2000 | Doherty, Jr. et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,127,363 A | 10/2000 | Doherty, Jr. et al. |
| 6,131,570 A | 10/2000 | Schuster et al. |
| 6,139,865 A | 10/2000 | Friend et al. |
| 6,156,753 A | 12/2000 | Doherty, Jr. et al. |
| 6,167,301 A | 12/2000 | Flower et al. |
| 6,197,350 B1 | 3/2001 | Yamagata et al. |
| 6,221,070 B1 | 4/2001 | Tu et al. |
| 6,221,870 B1 | 4/2001 | Pfaeffli et al. |
| 6,248,363 B1 | 6/2001 | Patel et al. |
| 6,256,533 B1 | 7/2001 | Yuzhakov et al. |
| 6,261,595 B1 | 7/2001 | Stanley et al. |
| 6,264,970 B1 | 7/2001 | Hata et al. |
| 6,267,981 B1 | 7/2001 | Okamoto et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,323,241 B1 | 11/2001 | Yeager et al. |
| 6,376,461 B1 | 4/2002 | Igari et al. |
| 6,403,597 B1 | 6/2002 | Wilson et al. |
| 6,419,961 B1 | 7/2002 | Igari et al. |
| 6,495,154 B1 | 12/2002 | Tam et al. |
| 6,548,490 B1 | 4/2003 | Doherty, Jr. et al. |
| 6,589,548 B1 | 7/2003 | Oh et al. |
| 6,613,358 B2 | 9/2003 | Randolph et al. |
| 6,693,135 B2 | 2/2004 | Yeager et al. |
| 6,699,500 B2 | 3/2004 | Okada et al. |
| 6,740,634 B1 | 5/2004 | Saikawa et al. |
| 6,780,400 B2 | 8/2004 | Rabinowitz et al. |
| 6,855,707 B2 | 2/2005 | Cincotta |
| 6,946,141 B2 | 9/2005 | Tam et al. |
| 7,105,571 B2 | 9/2006 | Yeager et al. |
| 7,126,012 B2 | 10/2006 | Lesieur et al. |
| 7,238,711 B1 | 7/2007 | Grainger et al. |
| 7,517,853 B2 | 4/2009 | Dong et al. |
| 7,572,883 B2 | 8/2009 | Culler et al. |
| 7,579,435 B2 | 8/2009 | Culler et al. |
| 7,650,848 B2 | 1/2010 | Brennan et al. |
| 7,666,877 B2 | 2/2010 | Baenteli et al. |
| 8,178,651 B2 | 5/2012 | Culler et al. |
| 8,324,386 B2 | 12/2012 | Culler et al. |
| 8,592,445 B2 | 11/2013 | Zhang et al. |
| 8,604,035 B2 | 12/2013 | Cook et al. |
| 8,618,107 B2 | 12/2013 | Barbosa et al. |
| 8,710,092 B2 | 4/2014 | Zhang et al. |
| 8,722,699 B2 | 5/2014 | Zhang et al. |
| 8,822,442 B2 | 9/2014 | Dong et al. |
| 8,841,448 B2 | 9/2014 | Cook et al. |
| 8,859,579 B2 | 10/2014 | Sewell |
| 8,883,831 B2 | 11/2014 | Bear et al. |
| 8,895,743 B2 | 11/2014 | Wu et al. |
| 8,927,567 B2 | 1/2015 | Cook et al. |
| 8,933,093 B2 | 1/2015 | Cook et al. |
| 8,946,420 B2 | 2/2015 | Cook et al. |
| 8,969,374 B2 | 3/2015 | Zhang et al. |
| 9,012,640 B2 | 4/2015 | Zhang et al. |
| 9,016,221 B2 | 4/2015 | Brennan et al. |
| 9,150,593 B2 | 10/2015 | Cook et al. |
| 9,365,591 B2 | 6/2016 | Cook et al. |
| 9,394,314 B2 | 7/2016 | Kellerman et al. |
| 9,657,020 B2 | 5/2017 | Armer et al. |
| 9,670,199 B2 | 6/2017 | Dosa et al. |
| 9,676,776 B2 | 6/2017 | Armer et al. |
| 9,777,016 B2 | 10/2017 | Armer et al. |
| 9,815,830 B2 | 11/2017 | Armer et al. |
| 9,938,277 B2 | 4/2018 | Armer et al. |
| 9,951,070 B2 | 4/2018 | Armer et al. |
| 10,246,458 B2 | 4/2019 | Armer et al. |
| 10,301,311 B2 | 5/2019 | Armer et al. |
| 10,308,651 B2 | 6/2019 | Armer et al. |
| 10,464,936 B2 | 11/2019 | Armer et al. |
| 10,703,753 B2 | 7/2020 | Armer et al. |
| 2006/0182792 A1 | 8/2006 | Richardsen et al. |
| 2010/0144754 A1 | 6/2010 | Peltz et al. |
| 2013/0158064 A1 | 6/2013 | Zhang et al. |
| 2013/0165469 A1 | 6/2013 | Cook et al. |
| 2013/0345253 A1 | 12/2013 | Zhang et al. |
| 2014/0045879 A1 | 2/2014 | Reiter et al. |
| 2014/0057896 A1 | 2/2014 | Barbosa et al. |
| 2014/0058108 A1 | 2/2014 | Horowski et al. |
| 2014/0073790 A1 | 3/2014 | Cook et al. |
| 2014/0094483 A1 | 4/2014 | Zhang et al. |
| 2014/0179705 A1 | 6/2014 | Armer et al. |
| 2014/0179706 A1 | 6/2014 | Armer et al. |
| 2014/0179707 A1 | 6/2014 | Armer et al. |
| 2014/0179730 A1 | 6/2014 | Wu et al. |
| 2014/0194434 A1 | 7/2014 | Cook et al. |
| 2014/0194435 A1 | 7/2014 | Cook et al. |
| 2015/0038525 A1 | 2/2015 | Wu et al. |
| 2015/0080422 A1 | 3/2015 | Bear et al. |
| 2015/0118327 A1 | 4/2015 | Sewell |
| 2015/0133456 A1 | 5/2015 | Armer et al. |
| 2015/0148371 A1 | 5/2015 | Cook et al. |
| 2015/0238487 A1 | 8/2015 | Armer et al. |
| 2018/0021334 A1 | 1/2018 | Marchant et al. |
| 2019/0169188 A1 | 6/2019 | Armer et al. |
| 2019/0337947 A1 | 11/2019 | Armer et al. |

FOREIGN PATENT DOCUMENTS

| | | |
|---|---|---|
| CA | 470573 A | 1/1951 |
| CN | 1541112 A | 10/2004 |
| CN | 103476402 A | 12/2013 |
| DE | 3413657 A1 | 10/1985 |
| DE | 3413660 A1 | 10/1985 |
| EP | 0252873 A1 | 1/1988 |
| EP | 0205608 B1 | 8/1989 |
| EP | 0351351 A2 | 1/1990 |
| EP | 0418990 B1 | 11/1993 |
| EP | 0427827 B1 | 1/1997 |
| EP | 0816364 A1 | 1/1998 |
| EP | 1303278 B1 | 11/2008 |
| EP | 2793583 A1 | 10/2014 |
| EP | 2838517 B1 | 10/2017 |
| GB | 1345546 A | 1/1974 |
| GB | 2116548 B | 3/1985 |
| GB | 2185743 A | 7/1987 |
| HU | 156385 | 4/1970 |

(56) References Cited

FOREIGN PATENT DOCUMENTS

| | | | |
|---|---|---|---|
| JP | S516998 A | 1/1976 | |
| JP | S51131898 A | 11/1976 | |
| JP | S5785385 A | 5/1982 | |
| JP | S5855483 A | 4/1983 | |
| JP | S60115580 A | 6/1985 | |
| JP | S60174783 A | 9/1985 | |
| JP | S60228478 A | 11/1985 | |
| JP | S62190184 A | 8/1987 | |
| JP | S63119483 A | 5/1988 | |
| JP | H02142789 A | 5/1990 | |
| JP | H03120277 A | 5/1991 | |
| JP | H04500681 A | 2/1992 | |
| JP | H1087662 A | 4/1998 | |
| JP | 2005506947 A | 3/2005 | |
| JP | 2008545725 A | 12/2008 | |
| WO | WO-9746239 A1 | 12/1997 | |
| WO | WO-2005025506 A2 | 3/2005 | |
| WO | WO-2010072774 A2 | 7/2010 | |
| WO | WO-2013095707 A1 | 6/2013 | |
| WO | WO-2013095708 A1 | 6/2013 | |
| WO | WO-2014078857 A1 | 5/2014 | |
| WO | WO-2014100354 A1 | 6/2014 | |
| WO | WO-2014186623 A2 | 11/2014 | |
| WO | WO-2016118539 A2 | 7/2016 | |
| WO | WO-2016118541 A1 | 7/2016 | |
| WO | WO-2018064465 A1 | 4/2018 | |
| WO | WO-2018223065 A1 | 12/2018 | |

OTHER PUBLICATIONS

Hironaka et al. Serotonin receptor antagonist inhibits monocrotaline-induced pulmonary hypertension and prolongs survival in rats. Cardiovascular Research 60:692-699 (2003).
Janssen et al. 5-HT2B Receptor Antagonists Inhibit Fibrosis and Protect from RV Heart Failure. BioMed Research International, vol. 2015, Article ID 438403 (2015). 8 pages. DOI: http://dx.doi.org/10.1155/2015/438403.
Monassier et al. Serotonin 5-HT2B Receptor Blockade Prevents Reactive Oxygen Species—Induced Cardiac Hypertrophy in Mice. Hypertension 52:301-307 (2008).
Co-pending U.S. Appl. No. 62/105,207, filed Jan. 20, 2015.
Co-pending U.S. Appl. No. 62/105,208, filed Jan. 20, 2015.
Co-pending U.S. Appl. No. 62/513,998, filed Jun. 1, 2017.
Ashford et al. A practical synthesis of cabergoline, Journal of Organic Chemistry, Oct. 4, 2002, 67(20):7147-7150.
Bernardi et al. Ergolines. VI. Epimerization of dihydrolysergic acid amides. Gazzetta Chimica Italiana 95.4 (1965): 375-83.
Blake et al. Qualitative analysis of lysergic acid diethylamide by means of the 10-hydroxy derivative. Analytical chemistry 45.2 (1973): 394-395.
Brambilla et al. Synthesis and nidation inhibitory activity of a new class of ergoline derivatives, European Journal of Medicinal Chemistry, Jul. 1, 1989, 24(4):421-426.
Brittain Polymorphism in Pharmaceutical Solids, (Brittain, H. ed.), Marcel Dekker, Inc. New York, (1999). Chapter 6, pp. 205-208.
Buchwald et al. Implantable Infusion Pump Management of Insulin Resistant Diabetes Mellitus. Surgery 88:507 (1980).
Burley Diversity-Optimized Route to the Ergoline Skeleton and the Efficient Synthesis of New HCV Inhibitors. San Diego State University, Spring 2013.
Calingaert. The Isomerization of Normal Heptane. Journal of the American Chemical Society 57:956-957 (1935).
Carstensen Drug Stability: Principles & Practice, 2d. Ed., Marcel Dekker, NY, NY, (1995), pp. 379-380.
CAS Registration Number: 782393-50-4, 4 other compounds, Registry (STN) [online], (Nov. 16, 2004.) 4 pages.
CAS Registry Nos. RN 32586-08-6, RN 27926-85-8, RN 25584-26-3, RN 25472-11-1, RN 25472-10-0, RN 25472-09-7, RN 25472-08-6, RN 25472-06-4, RN 25472-05-3, RN 25472-04-2, RN 25472-03-1, RN 25472-01-9, RN 2058-35-7, STN Entry Date Nov. 16, 1984.

Castro et al. Enhancement of oral absorption in selective 5-HT1D receptor agonists: fluorinated 3-[3-(piperidin-1-yl) propyl] indoles. Journal of medicinal chemistry 41.15 (1998): 2667-2670.
Cerny et al. Collection of Czechoslovak Chemical Communications. 31(8):3415-3418 (1966).
Cerny et al. Uber die syntheses der amide der o-dihydrolysergsaure(I) and 1-methyl-d-dihydrolysergsaure(I) durch kondenstation der primaren amine mit sauren. Coll. Czech. Chem. Commun. 31: 3415-3418 (1966).
Ennis et al. Isochroman-6-carboxamides as Highly Selective 5-HT1D Agonists: Potential New Treatment for Migraine without Cardiovascular Side Effects. J. Med. Chem. 41:2180-2183 (1998).
EP 16740618.0 Extended Search Report and Written Opinion dated May 29, 2018.
EP16740616.4 Office Action dated Sep. 18, 2019.
EP16740616.4 Extended European Search Report dated Jun. 12, 2018.
EP16740618.0 Office Action dated Jan. 24, 2020.
EP16740618.0 Office Action dated May 17, 2019.
Fabre et al. Modulation of bleomycin-induced lung fibrosis by serotonin receptor antagonists in mice. Eur Respir J 32:426-436 (2008).
Glennon et al. Higher-End Serotonin Receptors: 5-HT5, 5-HT6, 5-HT7, Journal of Medicinal Chemistry, Jun. 11, 2003, 46(14):2795-2812.
Goodson. Medical Applications of Controlled Release. vol. 2, pp. 115-138, 1984.
Guillory Methods Employed to Obtain Hydrate Forms. Polymorphism in Pharmaceutical Solids, (Brittain, H. ed.), Chapter 5, pp. 202-208 (1999).
Gupta et al. Structure-activity studies on LSD analogs using Van der Waals volume. European Journal of Medicinal Chemistry 16(5):446-448 (1981).
Ivanova et al. Functionalized Ergot-alkaloids as potential dopamine D3 receptor agonists for treatment of schizophrenia. Journal of Molecular Structure1029 (2012): 106-118.
Iwamura et al. Determination of methylergometrine and dihydroergotoxine in biological fluids. Journal of pharmacobio-dynamics 4.4 (1981): 275-281.
Jantschak et al. Pharmacological profile of 2-bromoterguride at human dopamine D2, porcine serotonin 5-hydroxytryptamine 2A, and alpha2c-adrenergic receptors, and its antipsychotic-like effects in rates. Journ. Pharmacol. Exper. Therap. 347(1): 57-68 (2013).
Kharasch et al. Ergotocin: the active principle of ergot responsible for the oral effectiveness of some ergot preparations on human uteri. Journal of the American Chemical Society 57.5 (1935): 956-957.
Königshoff. Increased expression of 5-hydroxytryptamine 2A/B receptors in idiopathic pulmonary fibrosis: a rationale for therapeutic intervention. Thorax 65:949-955 (2010).
Kumbar et al. Quantum Chemical Studies on Drug Actions: Correlation of Hallucinogenic and Anti-serotonin Activity of Lysergic Acid Derivatives with Quantum Chemical Data. Research Communications in Chemical Pathology and Pharmacology 6(1):65-100 (Jul. 1973).
Langer. New methods of drug delivery. Science. Sep. 28, 1990;249(4976):1527-33.
Löfdahl et al. 5-HT2B receptor antagonists attenuate myofibroblast differentiation and subsequent fibrotic responses in vitro and in vivo. Physiological Reports 4(15):e12873 (2016). 15 pages.
Mago, et al. Lysergic acid amides—HU156385, Chemical Abstracts Service, Columbus, Ohio, US; 1969, Database accession No. 1970:32105, 14 pages.
Merkel et al. Lumi-ergometrine—structural identification and occurrence in sclerotia. Mycotoxin Research (2012), 28(1), 59-66.
PCT/US2016/013978 Search Report and Written Opinion dated Oct. 13, 2016.
PCT/US2016/013980 Search Report and Written Opinion dated Jun. 6, 2016.
PCT/US2018/035701 International Search Report and Written Opinion dated Aug. 22, 2018.
Phebus. The effectiveness of a-dihydroergocryptine in migraine prophylaxis: a double-blind clinical study vs. placebo. Cephalalgia 17: 245 (1997).

(56) References Cited

OTHER PUBLICATIONS

Rothman. Evidence for Possible Involvement of 5-HT2B Receptors in the Cardiac Valvulopathy Associated With Fenfluramine and Other Serotonergic Medications. Circulation 102: 2836 (2000).

Saudek, et al. A preliminary trial of the programmable implantable medication system for insulin delivery. N Engl J Med. Aug. 31, 1989;321(9):574-9.

Schaerlinger. Agonist actions of dihydroergotamine at 5-HT2B and 5-HT2C receptors and their possible relevance to antimigraine efficacy. Br. J. Pharmacol. 140(2): 277-84, (2003).

Sefton, MV. Implantable pumps. Crit Rev Biomed Eng. 1987;14(3):201-40.

Semonsky et al. Collection symposium series, Chemistry of nucleic acid components spindleruv mlyn, czech republic; Sep. 3-9, 2005), Jan. 1, 1956, 21:382-391.

Slassi et al. 5-Alkyltryptamine derivatives as highly selective and potent 5-HT1D receptor agonists. Bioorganic & medicinal chemistry letters 10.15 (2000): 1707-1709.

Stadler et al. Ergot alkaloids. LIX. Selective reduction and oxidation reactions with lysergic acid derivatives. 2,3-Dihydro- and 12-hydroxylysergic acid amides, Helvetica Chimica Acta (1964), 47(3), 756-69.

Stoll et al. Ergot alkaloids. XXXVIII. Amides of stereoisomeric lysergic and dihydrolysergic acids. Helvetica Chimica Acta (1955), 38, 421-33.

U.S. Appl. No. 15/943,714 Notice of Allowance dated Aug. 29, 2018.

U.S. Appl. No. 15/943,714 Notice of Allowance dated Nov. 30, 2018.

U.S. Appl. No. 15/997,616 Notice of Allowance dated Feb. 8, 2019.

U.S. Appl. No. 16/016,474 Office Action dated Aug. 28, 2018.

U.S. Appl. No. 16/171,124 Notice of Allowance dated Jun. 28, 2019.

U.S. Appl. No. 16/171,124 Office Action dated Mar. 22, 2019.

U.S. Appl. No. 15/001,246 Notice of Allowance dated Mar. 1, 2017.

U.S. Appl. No. 15/001,246 Office Action dated Jul. 18, 2016.

U.S. Appl. No. 15/001,246 Office Action dated Oct. 28, 2016.

U.S. Appl. No. 15/001,252 Notice of Allowance dated Feb. 9, 2017.

U.S. Appl. No. 15/001,252 Notice of Allowance dated Jan. 25, 2017.

U.S. Appl. No. 15/001,252 Office Action dated Jun. 27, 2016.

U.S. Appl. No. 15/001,252 Office Action dated Oct. 14, 2016.

U.S. Appl. No. 15/448,951 Notice of Allowance dated Dec. 1, 2017.

U.S. Appl. No. 15/448,951 Office Action dated Apr. 11, 2017.

U.S. Appl. No. 15/448,951 Office Action dated Sep. 12, 2017.

U.S. Appl. No. 15/449,018 Notice of Allowance dated Dec. 15, 2017.

U.S. Appl. No. 15/586,244 Notice of Allowance dated Sep. 12, 2017.

U.S. Appl. No. 15/586,244 Notice of Allowance dated Sep. 26, 2017.

U.S. Appl. No. 15/586,255 Notice of Allowance dated Jun. 8, 2017.

U.S. Appl. No. 15/586,255 Notice of Allowance dated May 23, 2017.

U.S. Appl. No. 15/586,255 Notice of Allowance dated Sep. 5, 2017.

U.S. Appl. No. 16/016,474 Notice of Allowance dated Jan. 22, 2019.

U.S. Appl. No. 16/380,706 Office Action dated Sep. 20, 2019.

U.S. Appl. No. 15/449,018 Office Action dated Aug. 28, 2017.

U.S. Appl. No. 15/586,244 Office Action dated May 22, 2017.

Varagic et al. The effect of methysergide and x-irradiation on the barbiturate sleeping time in rats. International Journal of Radiation Biology and Related Studies in Physics, Chemistry and Medicine (1962), 5,559-65.

Voigt. Paper chromatography of the lumi-ergot alkaloids Pharmazie (1958), 13, 294-7.

Wilcox et al. CoMFA-Based Prediction of Agonist Affinities at Recombinant Wild Type versus Serine to Alanine Point Mutated D2 Dopamine Receptors, Journal of Medicinal Chemistry, Aug. 1, 2000, 43(16):3005-3019.

Co-pending U.S. Appl. No. 16/833,920, filed May 26, 2020.

EP16740616.4 Office Action dated Jun. 12, 2020.

EP16740618.0 Communication Pursuant to Article 94(3) EPC dated Jul. 16, 2020.

EP16740618.0 Result of Consultation Communication dated Jul. 28, 2020.

POLYCYCLIC COMPOUNDS AND USES THEREOF

CROSS-REFERENCE

This application is a continuation of U.S. patent application Ser. No. 15/997,616, filed Jun. 4, 2018, now U.S. Pat. No. 10,301,311, which is a continuation application of International Patent Application No. PCT/US2018/035701, filed Jun. 1, 2018, which claims the benefit of U.S. Provisional Patent Application No. 62/513,998, filed Jun. 1, 2017, each of which is entirely incorporated herein by reference.

BACKGROUND OF THE INVENTION

Medications comprising a compound having an ergoline scaffold have been used to ameliorate symptoms associated with various diseases and conditions, e.g., chronic migraines, postpartum hemorrhage, diabetic reset, hyperprolactinaemia, and Parkinson's disease. The naturally occurring and semi-synthetic ergoline compounds non-selectively bind to neurotransmitter receptors, e.g., dopamine, noradrenaline and serotonin receptors. The non-selective behavior of these ergolines leads to unwanted off-target effects that diminish the overall benefit of these compounds. There remains a need for compounds that bind selectively to neurotransmitter receptors to reduce undesired side-effects.

SUMMARY OF THE INVENTION

As described herein, the present disclosure provides polycyclic compounds and salts and their methods of use in the treatment of disease and disorders. In certain embodiments, the present disclosure provides polycyclic compounds and salts and methods of use thereof in the treatment of a symptom of Parkinson's Disease, restless leg syndrome, migraine, postpartum hemorrhage, senile dementia, diabetic reset, hyperprolactinaemia, or cardiovascular disease. The disclosure further provides methods of preparing compounds of the disclosure.

In one aspect, the present disclosure provides a compound represented by Formula (I):

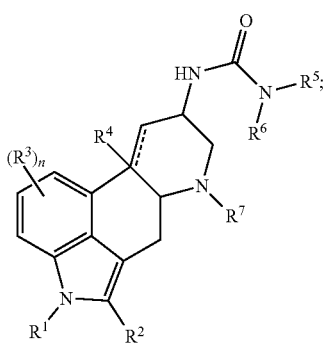

(I)

or a salt thereof, wherein:

------ represents an optional double bond;

$R^1$ is selected from hydrogen; and $C_1$-$C_3$ alkyl, $C_3$-$C_5$ cycloalkyl, $C_{2-4}$ alkenyl, $C_3$-$C_5$ cycloalkenyl, $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$ and —CN;

$R^2$ is selected from $C_1$-$C_3$ haloalkyl, and $C_3$-$C_5$ cycloalkyl, wherein $C_3$-$C_5$ cycloalkyl is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)R^{10}$, —$OC(O)R^{10}$, —$NO_2$, =O, =S, =$N(R^{10})$, and —CN;

$R^3$ is selected from halogen, $C_1$-$C_3$ alkyl, $C_1$-$C_3$ haloalkyl, —$OR^{10}$, —$SR^{10}$, —$N(R^{10})_2$, —$C(O)R^{10}$, —$C(O)OR^{10}$, —$OC(O)R^{10}$, —$NO_2$, and —CN;

$R^4$ is absent or selected from hydrogen and $OR^{10}$, wherein $R^4$ is absent when ------ is a double bond and $R^4$ is selected from hydrogen and $OR^{10}$ when ------ is a single bond;

$R^5$ is selected from $C_1$-$C_3$ alkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN, wherein when $R^2$ is selected from $C_1$ haloalkyl and ------ is a double bond, $R^5$ is $C_1$-$C_3$ alkyl optionally substituted with one or more substituents independently selected from —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;

$R^6$ is selected from $C_1$-$C_3$ alkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN, wherein when $R^2$ is $C_3$ cycloalkyl, $R^6$ is selected from substituted $C_1$-$C_3$ alkyl;

$R^7$ is selected from $C_1$-$C_3$ alkyl, $C_{2-4}$ alkenyl, and $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;

$R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, 2, and 3.

In certain embodiments, the compound of Formula (I) is represented by (IA):

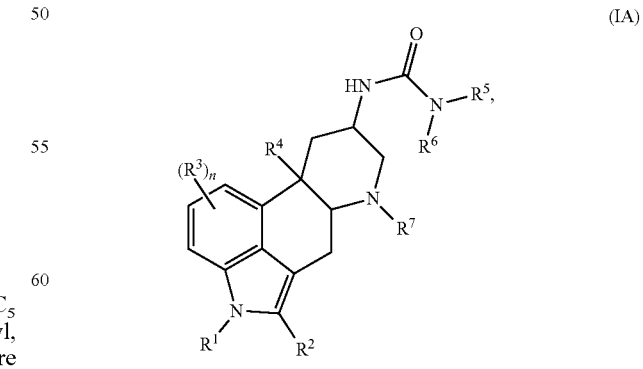

(IA)

or a salt thereof.

In one embodiment described herein, the compound of Formula (I) is represented by (IB):

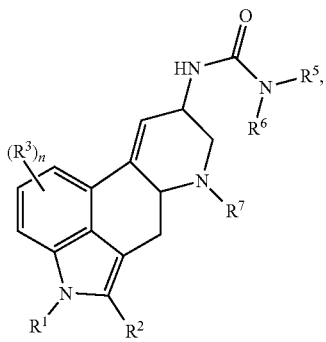

(IB)

or a salt thereof.

In certain embodiments for a compound or salt of any one of Formulas (I), (IA), or (IB), $R^2$ is selected from $C_1$-$C_3$ haloalkyl, e.g., $CF_3$. In certain embodiments, $R^2$ is selected from $C_3$-$C_5$ cycloalkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =$O$, =$S$, =$N(R^{10})$, and —$CN$. $R^2$ may be selected from optionally substituted cyclopropyl, optionally substituted cyclobutyl and optionally substituted cyclopentyl. In certain embodiments, $R^2$ is optionally substituted cyclopropyl, e.g., unsubstituted cyclopropyl. In certain embodiments, $R^2$ is selected from optionally substituted cyclobutyl and optionally substituted cyclopentyl.

In certain embodiments for a compound or salt of any one of Formulas (I), (IA), or (IB), n is 1. In certain embodiments for a compound or salt of any one of Formulas (I), (IA), or (IB), n is 0.

In certain embodiments for a compound or salt of any one of Formulas (I), (IA), or (IB), each $R^3$ is independently selected from halogen, $C_1$-$C_3$ alkyl, $C_1$-$C_3$ haloalkyl, —$OR^{10}$, —$SR^{10}$, —$N(R^{10})_2$, —$NO_2$, and —$CN$.

In certain embodiments for a compound or salt of any one of Formulas (I) or (IA), $R^4$ is selected from hydrogen and $OR^{10}$, e.g., —$OH$ and —$OCH_3$. In certain embodiments, $R^4$ is hydrogen.

In certain embodiments for a compound or salt of any one of Formulas (I), (IA), or (IB), when $R^2$ is optionally substituted $C_3$-$C_5$ cycloalkyl, $R^5$ is selected from $C_1$-$C_3$ alkyl optionally substituted with one or more substituents independently selected from halogen, —$OR^{10}$, —$SR^{10}$, —$N(R^{10})_2$, —$NO_2$, =$O$, and —$CN$, such as $R^5$ is unsubstituted $C_1$-$C_3$ alkyl. In certain embodiments, when $R^2$ is $C_1$ haloalkyl and ------ is a double bond, $R^5$ is selected from $C_1$-$C_3$ alkyl optionally substituted with one or more substituents independently selected from —$OR^{10}$, —$N(R^{10})_2$, —$NO_2$, =$O$, and —$CN$, such as $R^5$ is unsubstituted $C_1$-$C_3$ alkyl. In certain embodiments, when $R^2$ is $C_{2-3}$ haloalkyl, $R^5$ is selected from $C_1$-$C_3$ alkyl optionally substituted with one or more substituents independently selected from halogen, —$OR^{10}$, —$SR^{10}$, —$N(R^{10})_2$, —$NO_2$, =$O$, and —$CN$, such as $R^5$ is unsubstituted $C_1$-$C_3$ alkyl. In certain embodiments, $R^5$ is methyl, ethyl or propyl. In certain embodiments, $R^5$ is ethyl.

In certain embodiments for a compound or salt of any one of Formulas (I), (IA), or (IB), when $R^2$ is $C_1$-$C_3$ haloalkyl, $R^6$ is selected from $C_1$-$C_3$ alkyl optionally substituted with one or more substituents independently selected from halogen, —$OR^{10}$—$SR^{10}$, —$N(R^{10})_2$, —$NO_2$, =$O$, and —$CN$. In certain embodiments, when $R^2$ is $C_3$ cycloalkyl, $R^6$ is selected from $C_1$-$C_3$ alkyl substituted with one or more substituents independently selected from halogen, —$OR^{10}$, —$N(R^{10})_2$, —$NO_2$, =$O$, and —$CN$, such as $R^6$ is —$CH_2CF_3$. In certain embodiments, when $R^2$ is optionally substituted $C_4$-$C_5$ cycloalkyl, $R^6$ is selected from $C_1$-$C_3$ alkyl optionally substituted with one or more substituents independently selected from halogen, —$OR^{10}$, —$SR^{10}$, —$N(R^{10})_2$, —$NO_2$, =$O$, and —$CN$, such as $R^6$ is unsubstituted $C_1$-$C_3$ alkyl. In certain embodiments, $R^6$ is methyl, ethyl or propyl, each of which is substituted with at least one halogen. In certain embodiments, $R^6$ is methyl, ethyl or propyl, each of which is optionally substituted with at least one halogen. In certain embodiments, $R^6$ is —$CH_2CF_3$. In certain embodiments, $R^6$ is —$CH_2CH_3$.

In certain embodiments, for a compound or salt of any one of Formulas (I), (IA), or (IB), $R^7$ is selected from $C_1$-$C_3$ alkyl optionally substituted with one or more substituents independently selected from halogen, —$OR^{10}$, —$N(R^{10})_2$, —$NO_2$, =$O$, =$S$, and —$CN$. In certain embodiments, $R^7$ is methyl.

In certain embodiments, the compound of Formula (I) is represented by Formula (IC):

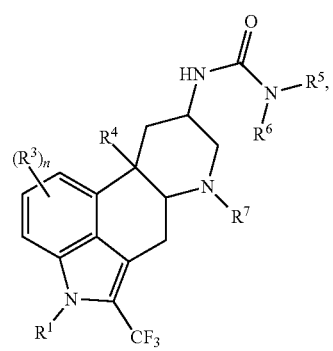

(IC)

or a salt thereof.

In certain embodiments, the compound of Formula (I) is represented by Formula (ID):

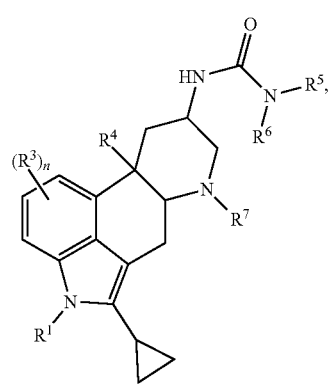

(ID)

or a salt thereof.

In certain embodiments, the compound of Formula (I) is represented by:

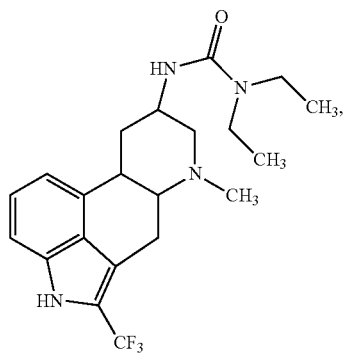

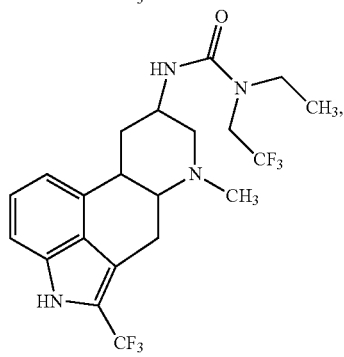

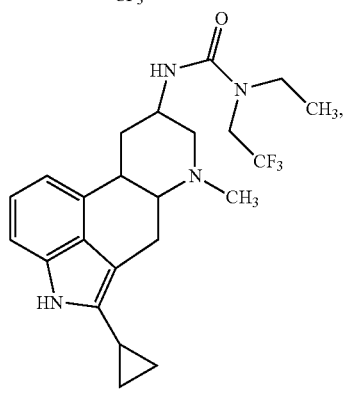

or a salt of any one thereof.

In one embodiments, the compound of Formula (I) is represented by:

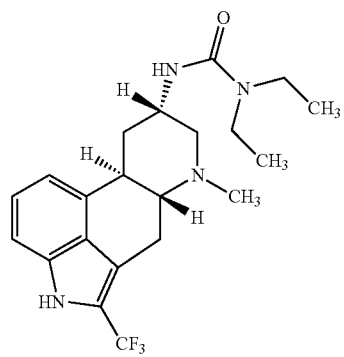 [SMILES: CCN(CC)C(=O)N[C@H]1C[C@@H]2c3cccc4[nH]c(C(F)(F)F)c(c34)C[C@H]2N(C)C1]

or a salt thereof.

In certain embodiments, the compound of Formula (I) is represented by:

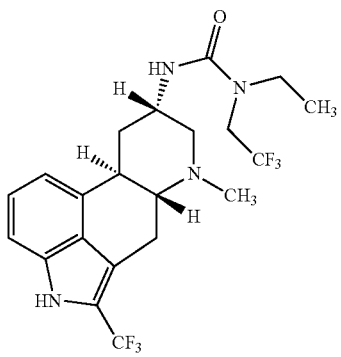 [SMILES: CCN(CC(F)(F)F)C(=O)N[C@H]1C[C@@H]2c3cccc4[nH]c(C(F)(F)F)c(c34)C[C@H]2N(C)C1]

or a salt thereof.

In certain embodiments, the compound of Formula (I) is represented by:

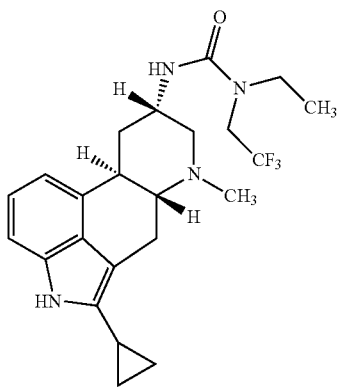 [SMILES: CCN(CC(F)(F)F)C(=O)N[C@H]1C[C@@H]2c3cccc4[nH]c(C5CC5)c(c34)C[C@H]2N(C)C1]

or a salt thereof.

In certain aspects, the present disclosure provides a pharmaceutical composition comprising a compound or salt of any one of Formulas (I), (IA), (IB), (IC), or (ID), and a pharmaceutically acceptable excipient. In certain embodiments, the present disclosure provides a method of treating or preventing a disease a disorder, comprising administering a compound or salt of any one of Formulas (I), (IA), (IB), (IC), or (ID), or a pharmaceutical composition thereof. In certain embodiments, the present disclosure provides a method of treating or preventing a symptom of Parkinson's Disease, restless leg syndrome, migraine, or cardiovascular disease comprising administering to a subject in need thereof, a compound or salt of any one of Formulas (I), (IA), (IB), (IC), or (ID), or a pharmaceutical composition thereof. In certain embodiments, the present disclosure provides a use of a compound or salt of any one of Formulas (I), (IA), (IB), (IC), or (ID), or a pharmaceutical composition described herein for the treatment or prevention of a symptom of Parkinson's Disease, restless leg syndrome, migraine, or cardiovascular disease.

In certain embodiments, the present disclosure provides a method of treating or preventing a disease or disorder, comprising administering a compound represented by Formula (IE):

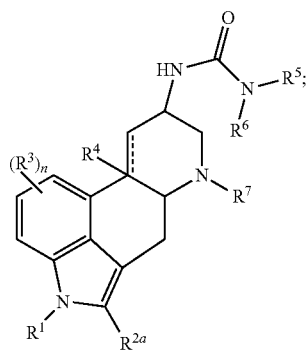

(IE)

or a salt thereof, to a subject in need thereof, wherein:
------ represents an optional double bond;

$R^1$ is selected from hydrogen; and $C_1$-$C_3$ alkyl, $C_3$-$C_5$ cycloalkyl, $C_{2-4}$ alkenyl, $C_3$-$C_5$ cycloalkenyl, $C_{2-4}$ alkynyl, each of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)O$R^{10}$, —OC(O)$R^{10}$, —NO$_2$, =O, =S, =N($R^{10}$), and —CN;

$R^{2a}$ is selected from halogen, $C_1$-$C_3$ haloalkyl and $C_3$-$C_5$ cycloalkyl, wherein $C_3$-$C_5$ cycloalkyl is optionally substituted with one or more substituents independently selected from halogen, —$R^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^1$, —NO$_2$, =O, =S, =N($R^{10}$), and —CN;

$R^3$ is selected from halogen, $C_1$-$C_3$ alkyl, $C_1$-$C_3$ haloalkyl, —$OR^{10}$, —$SR^{10}$, —N($R^{10}$)$_2$, —C(O)$R^{10}$, —C(O)O$R^{10}$, —OC(O)$R^{10}$, —NO$_2$, and —CN;

$R^4$ is absent or selected from hydrogen and $OR^{10}$, wherein $R^4$ is absent when ------ is a double bond and $R^4$ is selected from hydrogen and $OR^{10}$ when ------ is a single bond;

$R^5$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN, wherein when $R^{2a}$ is selected from $C_1$ haloalkyl and ------ is a double bond, $R^5$ is $C_1$-$C_3$ alkyl optionally substituted with one or more substituents independently selected from —$OR^{10}$, —$SR^{10}$, —C(O)N($R^{10}$)$_2$, —N($R^{10}$)$_2$, —S(O)$R^{10}$, —S(O)$R^{10}$, —C(O)$R^{10}$, —C(O)O$R^{10}$, —OC(O)$R^{10}$, —NO$_2$, =O, =S, =N($R^{10}$), and —CN;

$R^6$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN, wherein when $R^{2a}$ is $C_3$ cycloalkyl, $R^6$ is selected from substituted $C_1$-$C_3$ alkyl;

$R^7$ is selected from $C_1$-$C_3$ alkyl, $C_{2-4}$ alkenyl, and $C_{2-4}$ alkynyl, each of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^{10}$ is independently selected at each occurrence from hydrogen; and $C_1$-$C_3$ alkyl optionally substituted with one or more substituents independently selected from halogen, —OH, —OCH$_3$, —CF$_3$, —SH, —NH$_2$, —NO$_2$, and —CN; and n is selected from 0, 1, 2, and 3.

In certain embodiments, for a compound of Formula (IE), $R^{2a}$ is selected from halogen, e.g., Br. The compound of Formula (IE) may be represented by:

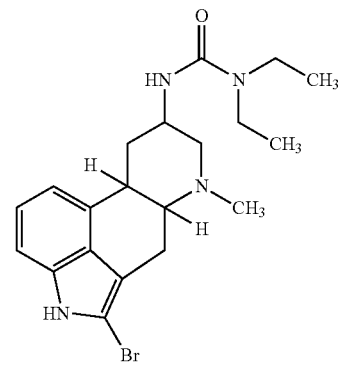 [SMILES: CCN(CC)C(=O)NC1CC2c3cccc4[nH]c(Br)c(c34)CC2N(C)C1]

or a salt thereof.

In certain embodiments, the disease or disorder is selected from a symptom of Parkinson's Disease, restless leg syndrome, migraine, or cardiovascular disease. In certain embodiments, the disease or disorder is selected from restless leg syndrome and a symptom of Parkinson's Disease.

In certain aspects, the present disclosure provides a process for preparing a compound represented by the formula:

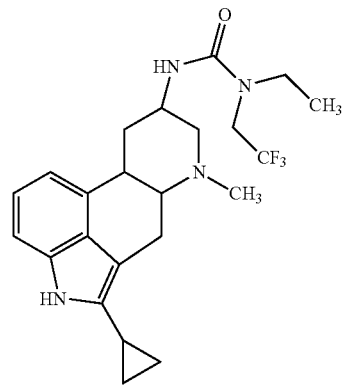 [SMILES: CCN(CC(F)(F)F)C(=O)NC1CC2c3cccc4[nH]c(C5CC5)c(c34)CC2N(C)C1]

comprising contacting a compound of formula 6:

6

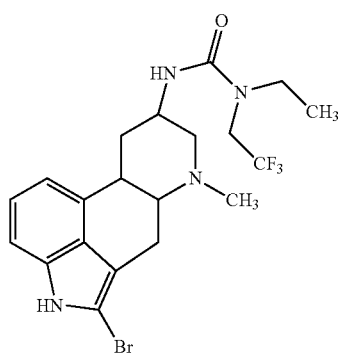

with cyclopropyl boronic acid under cross-coupling conditions.

In certain embodiments, the present disclosure provides a process for preparing a compound of Formula 6:

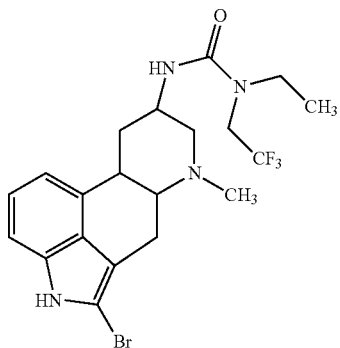

6 comprising contacting a compound of formula 5:

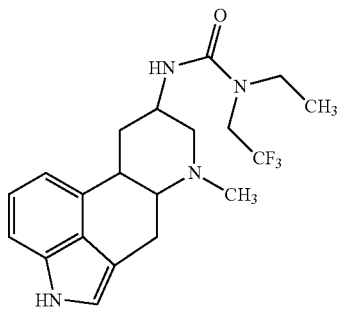

5 with a brominating agent under suitable halogenation conditions.

In certain aspects, the present disclosure provides a process for preparing a compound of formula 5:

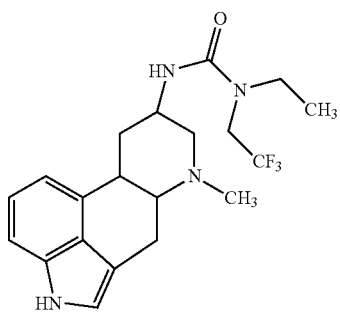

5 comprising contacting a compound of formula 4:

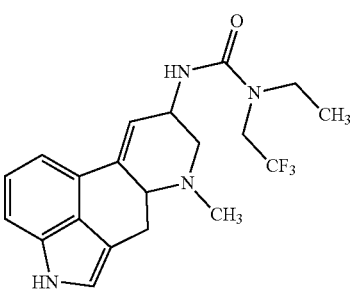

4 with $H_2$ under suitable hydrogenation conditions.

In certain aspects, the present disclosure provides a process for preparing a compound of formula 4:

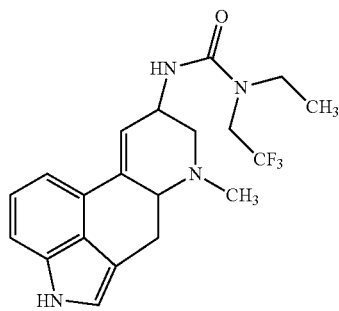

4 comprising contacting a compound of formula 3:

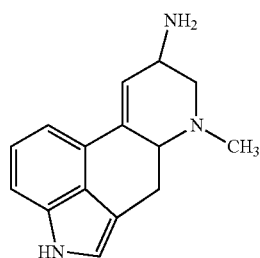

3 with ethyl(2,2,2-trifluoroethyl)amine and triphosgene under suitable conditions to form a urea derivative.

In certain aspects, the present disclosure provides a process for preparing a compound of the formula:

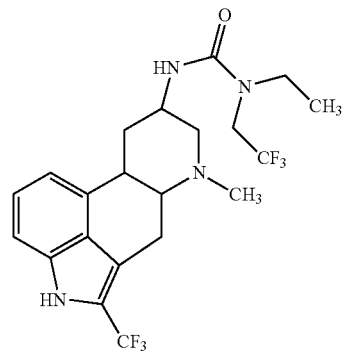 [SMILES: CCN(CC(F)(F)F)C(=O)NC1CC2c3cccc4[nH]c(C(F)(F)F)c(c34)CC2N(C)C1]

comprising contacting a compound of formula 5:

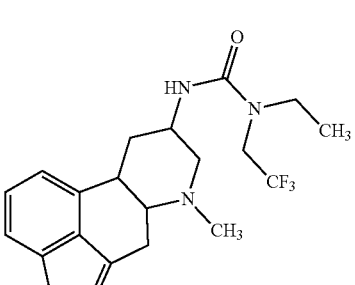

5 with a trifluoromethylation reagent under suitable trifluoromethylation conditions.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

All publications, patents, and patent applications mentioned in this specification are herein incorporated by reference to the same extent as if each individual publication, patent, or patent application was specifically and individually indicated to be incorporated by reference.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001 (and other editions, including 7$^{th}$ Ed.: 2013). The foregoing are incorporated by reference in their entirety.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

Unless otherwise indicated, a substituent connected by a bond drawn from the center of a ring means that the substituent can be bonded to any position in the ring. In example (i) below, for instance, J$^w$ can be bonded to any position on the pyridyl ring. For bicyclic rings, a bond drawn through both rings indicates that the substituent can be bonded from any position of the bicyclic ring. In example (ii) below, for instance, J$^w$ can be bonded to the 5-membered ring (on the nitrogen atom, for instance), and to the 6-membered ring. Examples (i) and (ii):

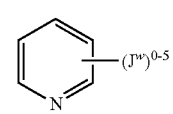

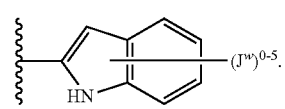

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —$CH_2$-cyclopropyl, $CH_2CH_2CH(CH_3)$-cyclohexyl.

"Alkyl" refers to a straight or branched hydrocarbon chain radical consisting solely of carbon and hydrogen atoms, containing no unsaturation, and preferably having from one to three carbon atoms (i.e., $C_1$-$C_3$ alkyl). In certain embodiments, an alkyl comprises one to two carbon atoms (i.e., $C_1$-$C_2$ alkyl). In other embodiments, an alkyl comprises one carbon atom (i.e., $C_1$ alkyl). In certain embodiments, the alkyl group is selected from methyl, ethyl, 1-propyl (n-propyl), and 1-methylethyl (iso-propyl). The alkyl is attached to the rest of the molecule by a single bond. Unless stated otherwise specifically in the specification, an alkyl group is optionally substituted by one or more substituents such as those substituents described herein.

"Alkenyl" refers to a straight or branched hydrocarbon chain radical group consisting solely of carbon and hydrogen atoms, containing at least one carbon-carbon double bond, and preferably having from two to four carbon atoms (i.e., $C_2$-$C_4$ alkenyl). In certain embodiments, an alkenyl comprises two to three carbon atoms (i.e., $C_2$-$C_3$ alkenyl). The alkenyl may be attached to the rest of the molecule by a single bond, for example, ethenyl (i.e., vinyl), prop-1-enyl (i.e., allyl), and the like. Unless stated otherwise specifically in the specification, an alkenyl group is optionally substituted by one or more substituents such as those substituents described herein.

"Alkynyl" refers to a straight or branched hydrocarbon chain radical group consisting solely of carbon and hydrogen atoms, containing at least one carbon-carbon triple bond, and preferably having from two to four carbon atoms (i.e., $C_2$-$C_4$ alkynyl). In certain embodiments, an alkynyl comprises two to three carbon atoms (i.e., $C_2$-$C_3$ alkynyl). The alkynyl may be attached to the rest of the molecule by a single bond, for example, ethynyl, propynyl, and the like. Unless stated otherwise specifically in the specification, an alkynyl group is optionally substituted by one or more substituents such as those substituents described herein.

The term "$C_{x-y}$" when used in conjunction with a chemical moiety, such as alkyl, alkenyl, or alkynyl is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, cyclobutyl, and cyclopentyl.

The term "cycloalkyl" refers to a cyclic hydrocarbon radical consisting solely of carbon and hydrogen atoms, containing no unsaturation, and preferably having from three to six carbon atoms (i.e., $C_3$-$C_6$ cycloalkyl). In certain embodiments, a cycloalkyl comprises three to five carbon atoms (i.e., $C_3$-$C_5$ cycloalkyl). In certain embodiments, a cycloalkyl comprises four or five carbon atoms (i.e., $C_4$-$C_5$ cycloalkyl). In certain embodiments, a cycloalkyl comprises three carbon atoms (i.e., $C_3$ cycloalkyl). In certain embodiments, the cycloalkyl group is selected from cyclopropyl, cyclobutyl, cyclopentyl, and cyclohexyl. The cycloalkyl is attached to the rest of the molecule by a single bond. Unless stated otherwise specifically in the specification, a cycloalkyl group is optionally substituted by one or more substituents such as those substituents described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2imidazolidinyl, 4-imidazolidinyl, 5-imidazolidinyl, indolinyl, tetrahydroquinolinyl, tetrahydroisoquinolinyl, and 1,3-dihydro-imidazol-2-one.

The term "heterocycloalkyl" refers to a cyclic hydrocarbon radical consisting of carbon and hydrogen atoms and one or more heteroatoms, containing no unsaturation, and preferably having from three to six ring atoms (i.e., 3 to 6-membered ring). In certain embodiments, a heterocycloalkyl comprises three to five ring atoms (i.e., 3 to 5-membered ring). In certain embodiments, a heterocycloalkyl comprises four or five ring atoms (i.e., 4 to 5-membered ring). The heterocycloalkyl is attached to the rest of the molecule by a single bond. Unless stated otherwise specifically in the specification, a heterocycloalkyl group is optionally substituted by one or more substituents such as those substituents described herein.

Cyclic groups, (e.g. cycloaliphatic and heterocycles), can be linearly fused, bridged, or spirocyclic.

The term "heteroatom" refers to a non-carbon atom such as oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has at least one double or triple bond.

The term "alkoxy", or "thioalkyl", as used herein, refers to an alkyl group, as previously defined, attached through an oxygen ("alkoxy") or sulfur ("thioalkyl") atom to the remainder of the compound.

The terms "haloalkyl", "haloalkenyl", "haloalkynyl", "haloaliphatic", and "haloalkoxy" mean alkyl, alkenyl, alkynyl, aliphatic or alkoxy, respectively, each substituted with one or more halogen atoms. The terms includeperhalogenated groups, such as perfluorinated alkyl groups, such as —CF$_3$ and CF$_2$CF$_3$.

The terms "halogen", "halo", and "hal" include F, Cl, Br, or I.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents such as those substituents described herein.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted such as those substituents described herein. Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, 4-isoquinolinyl), benzothiolane, or benzodithiane.

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

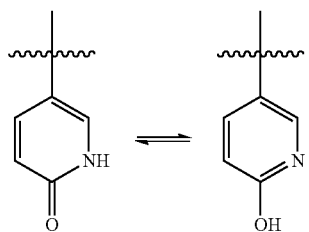 [SMILES: *c1ccc(=O)[nH]c1 ; *c1ccc(O)nc1]

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds.

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopes. For example, compounds having the present structures except for the replacement of hydrogen by deuterium or tritium, or the replacement of a carbon by a $^{13}$C- or $^{14}$C-enriched carbon are within the scope of this invention. As would be understood by one skilled in the art, compounds may have a natural variation in isotopic abundance or may be enriched. In certain embodiments, such compounds are useful, for example, as analytical tools or probes in biological assays. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods. Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

As used herein, the term "pharmaceutically acceptable solvate," is a solvate formed from the association of one or more pharmaceutically acceptable solvent molecules to one of the compounds described herein.

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

An "agonist" refers to a molecule having an affinity for and stimulates physiological activity at cell receptors normally stimulated by naturally occurring substances.

An "antagonist" refers to a molecule capable of neutralizing, blocking, inhibiting, abrogating, reducing or interfering with the activities of a particular or specified protein or other biomolecule. Antagonists may bind to one or more receptors in the case of a ligand, or binding to one or more ligands in case of a receptor.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

The term "coupling reaction", as used herein, refers to a reaction in which a carbon-carbon bond is formed with the aid of a metal catalyst. Usually, one of the carbon atoms is bonded to a functional group (a "cross-coupling group") while the other carbon atom is bonded to a halogen. Examples of coupling reactions include, but are not limited to, Suzuki couplings, Stille couplings, Negishi and Buchwald couplings.

The term "coupling group", as used herein, refers to a functional group capable of reacting with another functional group (e.g. halo) in a coupling reaction to form a carbon-carbon ("C—C") bond or a carbon-nitrogen ("C—N") bond. In some embodiments, the C—C bond is formed between two aromatic groups.

The term "coupling condition", as used herein, refers to the chemical conditions (e.g. temperature, length of time of reaction, volume of solvent required) required in order to enable the coupling reaction to occur.

Examples of coupling groups and their respective coupling conditions include, but are not limited to, boronic acids and boronic esters with Suzuki coupling conditions, $SnBu_3$ with Stille coupling conditions, and ZnX with Negishi coupling conditions.

All three of these coupling conditions typically involve the use of a catalyst, a suitable solvent, and optionally a base. Suzuki coupling conditions involve the use of a palladium catalyst, a suitable base and a suitable solvent. Examples of suitable palladium catalysts include, but are not limited to, $PdCl_2(PPh_3)_2$, $Pd(Ph_3)_4$, and $PdCl_2(dppf)$. Suitable bases include, but are not limited to, $K_2CO_3$ and $Na_2CO_3$. Suitable solvents include, but are not limited to, tetrahydrofuran, toluene, and ethanol.

Stille coupling conditions involve the use of a catalyst (usually palladium, but sometimes nickel), a suitable solvent, and other optional reagents. Examples of suitable catalysts include, but are not limited to, $PdCl_2(PPh_3)_2$, $Pd(Ph_3)_4$, and $PdCl_2(dppf)$. Suitable solvents include, but are not limited to, tetrahydrofuran, toluene, and dimethylformamide.

Negishi coupling conditions involve the use of a catalyst (palladium or nickel) and a suitable solvent. Examples of suitable catalysts include, but are not limited to $Pd_2(dba)_3$, $Ni(PPh_3)_2Cl_2$, $PdCl_2(PPh_3)_2$, and $Pd(Ph_3)_4$. Suitable solvents include, but are not limited to, tetrahydrofuran, toluene, and dimethylformamide. Suzuki, Stille, and Negishi conditions are known to one skilled in the art and are described in more detail in a variety of references, including "March's Advanced Organic Chemistry".

Buchwald coupling conditions involve the use of a palladium catalyst, a suitable base and a suitable solvent. Examples of suitable palladium catalysts include, but are not limited to, $Pd(OAc)_2$ with xanthphos, $PdCl2(PPh_3)_2$, $Pd(Ph_3)_4$, and $PdCl_2(dppf)$. Suitable bases include, but are not limited to, $Cs_2CO_3$, $K_2CO_3$ and $Na_2CO_3$. Suitable solvents include, but are not limited to, dioxane, tetrahydrofuran, toluene, and ethanol.

As would be understood by one skilled in the art, coupling groups are formed from coupling group precursors. A "coupling group precursor" is a reagent or group of reagents used to form a cross-coupling group. Examples include, but are not limited to, bis(pinacolato)diborane for the formation of boronate esters, trimethylborates for the formation of boronic acids, $Bu_3SnCl$ for the formation of stannanes, and $ZnCl_2$ for the formation zincates in Negishi coupling reactions. Examples of suitable coupling group formation conditions include, but are not limited to, making boronic esters via palladium-mediated catalysis; making boronic acids by hydrolyzing boronic esters; making stannanes via a two step process: 1) halogen metal exchange followed by 2) transmetallation with Bu3SnCl; and making zincates via a two step process: 1) halogen metal exchange followed by 2) addition of $ZnCl_2$.

An "individual," "subject," or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

"Prevent", "preventing" and the like can refer to the prevention of the disease or condition or symptoms thereof, e.g., prevent migraine onset or Parkinson's symptoms, in the patient. For example, if an individual at risk of developing a migraine is administered a compound or salt of the present disclosure and does not later develop the migraine, then the migraine has been prevented, at least over a period of time, in that individual. Preventing can also refer to preventing re-occurrence of a disease or condition in a patient that has previously been treated for the disease or condition, e.g., by preventing relapse.

"Treating" or "treatment" of any disease or disorder refers, in some embodiments, to managing or to ameliorating the disease or disorder (i.e., arresting or reducing any aspect of the disease or at least one of the clinical symptoms thereof). Treatment can also refer to the lessening of the severity and/or the duration of one or more symptoms of a disease or disorder. In a further feature, the treatment rendered has lower potential for long term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both.

A "medicament" is an active drug that has been manufactured for the treatment of a disease, disorder, or condition.

An "effective amount" refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount may be less than the therapeutically effective amount.

"Patient response" or "response" can be assessed using any endpoint indicating a benefit to the patient, including, without limitation, (1) inhibition, to some extent, of disease progression, including stabilization, slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

Compounds

In one aspect, the present disclosure provides a compound represented by Formula (I):

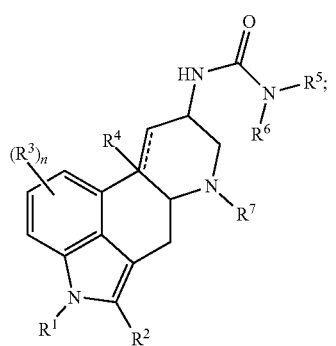

(I)

or a salt thereof, wherein:

------ represents an optional double bond;

$R^1$ is selected from hydrogen; and $C_1$-$C_3$ alkyl, $C_3$-$C_5$ cycloalkyl, $C_{2-4}$ alkenyl, $C_3$-$C_5$ cycloalkenyl, $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$, and —CN;

$R^2$ is selected from $C_1$-$C_3$ haloalkyl and $C_3$-$C_5$ cycloalkyl, wherein $C_3$-$C_5$ cycloalkyl is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;

$R^3$ is selected from halogen, $C_1$-$C_3$ alkyl, $C_1$-$C_3$ haloalkyl, —$OR^{10}$, —$SR^{10}$, —$N(R^{10})_2$, —$C(O)R^{10}$, —$C(O)OR^{10}$, —$OC(O)R^{10}$, —$NO_2$, and —CN;

$R^4$ is absent or selected from hydrogen and $OR^{10}$, wherein $R^4$ is absent when ------ is a double bond and $R^4$ is selected from hydrogen and $OR^{10}$ when ------ is a single bond;

$R^5$ is selected from $C_1$-$C_3$ alkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN, wherein when $R^2$ is selected from $C_1$ haloalkyl and ------ is a double bond, $R^5$ is $C_1$-$C_3$ alkyl optionally substituted with one or more substituents independently selected from —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;

$R^6$ is selected from $C_1$-$C_3$ alkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN, wherein when $R^2$ is $C_3$ cycloalkyl, $R^6$ is selected from substituted $C_1$-$C_3$ alkyl;

$R^7$ is selected from $C_1$-$C_3$ alkyl, $C_{2-4}$ alkenyl, and $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;

$R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, 2, and 3.

In certain embodiments, the compound of Formula (I) is represented by (IA):

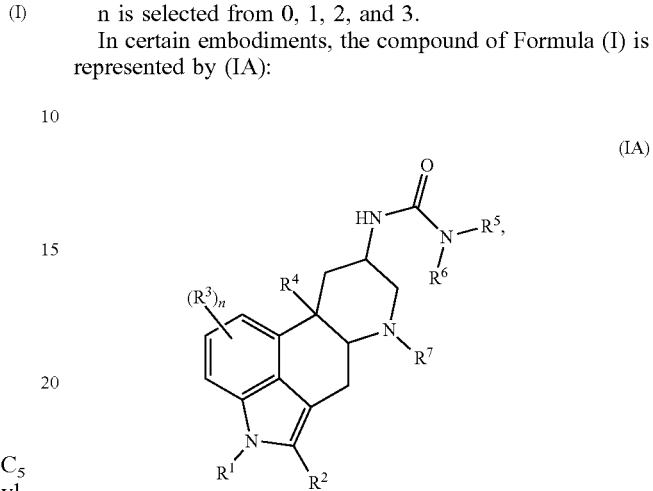

(IA)

or a salt thereof.

In certain embodiments, the compound of Formula (I) is represented by (IB):

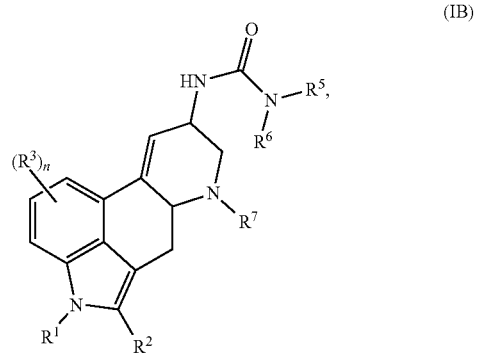

(IB)

a salt thereof.

In some embodiments for a compound of Formula (I), (IA), or (IB), $R^1$ is selected from hydrogen; and $C_1$-$C_3$ alkyl, $C_3$-$C_5$ cycloalkyl, $C_{2-4}$ alkenyl, $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$, and —CN. In some embodiments, $R^1$ is selected from hydrogen; and $C_1$-$C_3$ alkyl, $C_3$-$C_5$ cycloalkyl, $C_{2-4}$ alkenyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$, and —CN. In some embodiments, $R^1$ is selected from hydrogen; and $C_1$-$C_3$ alkyl, $C_3$-$C_5$ cycloalkyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$, and —CN. In certain embodiments, $R^1$ is selected from hydrogen; and $C_1$-$C_3$ alkyl, $C_3$-$C_5$ cycloalkyl, each of which is optionally substituted with one or more substituents independently selected from halogen, —$OR^{10}$, —C(O)N($R^{10}$)$_2$, —N($R^{10}$)$_2$, —C(O)$OR^{10}$, —OC(O)$R^{10}$, —$NO_2$, =O, =N($R^{10}$), and —CN. In certain embodiments, $R^1$ is selected from hydrogen; and $C_1$-$C_3$ alkyl, $C_3$-$C_5$ cycloalkyl, each of which is optionally substituted with one or more substituents independently selected from halogen, —$OR^{10}$, —N($R^{10}$)$_2$, —$NO_2$, =O, =N($R^{10}$), and —CN. In certain embodiments, $R^1$ is selected from hydrogen; and $C_1$-$C_3$ alkyl, $C_3$-$C_5$ cycloalkyl, each of which is optionally substituted with one or more substituents independently selected from halogen, —$OR^{10}$, —$NO_2$, =O, and —CN.

In certain embodiments for a compound of Formula (I), (IA), or (IB), $R^1$ is hydrogen. In other embodiments for a compound of Formula (I), (IA), or (IB), $R^1$ is $C_1$-$C_3$ alkyl which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$OR^{10}$, —OC(O)$R^{10}$, —$NO_2$, =O, =S, =N($R^{10}$), and —CN. In certain embodiments, $R^1$ is $C_1$-$C_3$ alkyl which is optionally substituted with one or more substituents independently selected from halogen, —$OR^{10}$, —C(O)N($R^{10}$)$_2$, —N($R^{10}$)$_2$, —C(O)$OR^{10}$, —OC(O)$R^{10}$, —$NO_2$, =O, =N($R^{10}$), and —CN. In certain embodiments, $R^1$ is $C_1$-$C_3$ alkyl which is optionally substituted with one or more substituents independently selected from halogen, —$OR^{10}$, —N($R^{10}$)$_2$, —$NO_2$, =O, =N($R^{10}$), and —CN.

In other embodiments for a compound of Formula (I), (IA), or (IB), $R^1$ is $C_3$-$C_5$ cycloalkyl which is optionally substituted with one or more substituents independently selected from halogen, $OR^{10}$, —$SR^{10}$, —C(O)N($R^{10}$)$_2$, —N($R^{10}$)$_2$, —S(O)$R^{10}$, —S(O)$_2R^{10}$, —C(O)$OR^{10}$, —OC(O)$R^{10}$, —$NO_2$, =O, =S, =N($R^{10}$), and —CN. In certain embodiments, $R^1$ is $C_3$-$C_5$ cycloalkyl which is optionally substituted with one or more substituents independently selected from halogen, $OR^{10}$, —C(O)N($R^{10}$)$_2$, —N($R^{10}$)$_2$, —C(O)$OR^{10}$, —OC(O)$R^{10}$, —$NO_2$, =O, =N($R^{10}$), and —CN. In certain embodiments, $R^1$ is $C_3$-$C_5$ cycloalkyl which is optionally substituted with one or more substituents independently selected from halogen, $OR^{10}$, —N($R^{10}$)$_2$, —$NO_2$, =O, =N($R^{10}$), and —CN. In certain embodiments, $R^1$ is $C_3$-$C_5$ cycloalkyl which is optionally substituted with one or more substituents independently selected from halogen, $OR^{10}$, —$NO_2$, =O, and —CN.

In certain embodiments for a compound of Formula (I), (IA), or (IB), $R^2$ is selected from $C_1$-$C_3$ haloalkyl. In certain embodiments, $R^2$ is selected from $C_1$ haloalkyl, $C_2$ haloalkyl, and $C_3$ haloalkyl. In certain embodiments, $R^2$ is $C_1$ haloalkyl. In certain embodiments, $R^2$ is selected from $CF_3$.

In certain embodiments, $R^2$ is selected from $C_3$-$C_5$ cycloalkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$OR^{10}$, —OC(O)$R^{10}$, —$NO_2$, =O, =S, =N($R^{10}$), and —CN. In certain embodiments, $R^2$ is selected from cyclopropyl, cyclobutyl and cyclopentyl. In certain embodiments, $R^2$ is selected from cyclopropyl, cyclobutyl and cyclopentyl, any of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$OR^{10}$, —OC(O)$R^{10}$, —$NO_2$, =O, =S, =N($R^{10}$), and —CN.

In certain embodiments, $R^2$ is selected from cyclopropyl optionally substituted with one or more substituents independently selected from halogen, —$OR^{10}$, —C(O)N($R^{10}$)$_2$, —N($R^{10}$)$_2$, —C(O)$R^{10}$, —C(O)$OR^{10}$, —OC(O)$R^{10}$, —$NO_2$, =O, =N($R^{10}$), and —CN. In certain embodiments, $R^2$ is selected from cyclopropyl optionally substituted with one or more substituents independently selected from halogen, —$OR^{10}$, —N($R^{10}$)$_2$, —$NO_2$, =O, =N($R^{10}$), and —CN. In further embodiments, $R^2$ is selected from cyclopropyl optionally substituted with one or more substituents independently selected from halogen, —$OR^{10}$, —$NO_2$, =O, and —CN. In further embodiments, wherein $R^2$ is unsubstituted cyclopropyl.

In certain embodiments, $R^2$ is selected from optionally substituted cyclobutyl and optionally substituted cyclopentyl. In certain embodiments, $R^2$ is selected from cyclobutyl and cyclopentyl, either of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$OR^{10}$, —OC(O)$R^{10}$, —$NO_2$, =O, =S, =N($R^{10}$), and —CN. In certain embodiments, $R^2$ is selected from cyclobutyl and cyclopentyl optionally substituted with one or more substituents independently selected from halogen, —$OR^{10}$, —C(O)N($R^{10}$)$_2$, —N($R^{10}$)$_2$, —C(O)$R^{10}$, —C(O)$OR^{10}$, —OC(O)$R^{10}$, —$NO_2$, =O, =N($R^{10}$), and —CN.

In certain embodiments for a compound of Formula (I), (IA), or (IB), n is selected from 0, 1, and 2. In certain embodiments, n is selected from 0 and 1. In some embodiments, n is 3. In some embodiments, n is 2. In some embodiments, n is 1. In some embodiments, n is 0.

In certain embodiments for a compound of Formula (I), (IA), or (IB), $R^3$ is selected from halogen, $C_1$-$C_3$ alkyl, $C_1$-$C_3$ haloalkyl, —$OR^{10}$, —$SR^{10}$, —N($R^{10}$)$_2$, —$NO_2$, and —CN. In certain embodiments, $R^3$ is selected from halogen, $C_1$-$C_3$ alkyl, $C_1$-$C_3$ haloalkyl, —$NO_2$, and —CN.

In certain embodiments for a compound of Formula (I) or (IA), $R^4$ is selected from hydrogen and —$OR^{10}$, e.g., —OH or —$OCH_3$. In a certain embodiments, $R^4$ is hydrogen. In certain embodiments, $R^4$ is selected from $C_1$-$C_3$alkoxy optionally substituted with one or more substituents independently selected from halogen, —OH, —$OCH_3$, —$CF_3$, —SH, —$NH_2$, —$NO_2$, and —CN.

In certain embodiments for a compound of Formula (I), (IA), or (IB), when $R^2$ is optionally substituted $C_3$-$C_5$ cycloalkyl, $R^5$ is selected from $C_1$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$R^{10}$—OC(O)$R^{10}$, —$NO_2$, =O, =S, =N($R^{10}$), and —CN. In certain embodiments, when $R^2$ is optionally substituted $C_3$-$C_5$ cycloalkyl, $R^5$ is selected from $C_2$ alkyl optionally substituted with one or more substituents independently selected from halogen, —$OR^{10}$. —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$R^{10}$, —OC(O)$R^{10}$, —$NO_2$, =O, =S, =N($R^{10}$), and —CN. In certain embodiments, when $R^2$ is optionally substituted $C_3$-$C_5$ cycloalkyl, $R^5$ is selected from $C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)$OR^{10}$, —OC(O)$R^{10}$, —$NO_2$, =O, =S, =N($R^{10}$), and —CN.

In certain embodiments for a compound of Formula (I), (IA), or (IB), when $R^2$ is optionally substituted $C_3$-$C_5$ cycloalkyl, $R^5$ is selected from $C_1$-$C_3$ alkyl optionally substituted with one or more substituents independently selected from halogen, —$OR^{10}$, —$SR^{10}$, —N($R^{10}$)$_2$, —$NO_2$, =O and —CN. In certain embodiments, when $R^2$ is optionally substituted $C_3$-$C_5$ cycloalkyl, $R^5$ is unsubstituted $C_1$-$C_3$ alkyl. In certain embodiments, when $R^2$ is optionally substituted $C_3$-$C_5$ cycloalkyl, $R^5$ is methyl, ethyl or propyl. In certain embodiments, when $R^2$ is optionally substituted $C_3$-$C_5$ cycloalkyl, $R^5$ is methyl. In certain embodiments, when $R^2$ is optionally substituted $C_3$-$C_5$ cycloalkyl, $R^5$ is ethyl. In certain embodiments, when $R^2$ is optionally substituted $C_3$-$C_5$ cycloalkyl, $R^5$ is propyl.

In certain embodiments for a compound of Formula (I), (IA), or (TB), when $R^2$ is $C_1$ haloalkyl, $R^5$ is $C_1$-$C_3$ alkyl optionally substituted with one or more substituents independently selected from —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, when $R^2$ is $C_1$ haloalkyl, $R^5$ is selected from $C_1$-$C_3$ alkyl optionally substituted with one or more substituents independently selected from —$OR^{10}$, —$SR^{10}$, —N($R^{10}$)$_2$, —NO$_2$, =O, and —CN. In certain embodiments, when $R^2$ is $C_1$ haloalkyl, $R^5$ is selected from unsubstituted $C_1$-$C_3$ alkyl. In certain embodiments, when $R^2$ is $C_1$ haloalkyl, $R^5$ is selected from methyl, ethyl or propyl. In certain embodiments, when $R^2$ is $C_1$ haloalkyl, $R^5$ is ethyl.

In certain embodiments for a compound of Formula (I), (IA), or (IB), when $R^2$ is $C_{2-3}$ haloalkyl, $R^5$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —OC(O)$R^{10}$, —NO$_2$, =O, =S, =N($R^{10}$), and —CN. In certain embodiments, when $R^2$ is $C_{2-3}$ haloalkyl, $R^5$ is selected from $C_1$-$C_3$ alkyl optionally substituted with one or more substituents independently selected from halogen, —$OR^{10}$, —$SR^{10}$, —N($R^{10}$)$_2$, —NO$_2$, =O, and —CN. In certain embodiment, $R^5$ is unsubstituted $C_1$-$C_3$ alkyl. In certain embodiments, $R^5$ is methyl, ethyl or propyl. In certain embodiments, $R^5$ is methyl. In certain embodiments, $R^5$ is ethyl. In certain embodiments, $R^5$ is propyl.

In certain embodiments for a compound of Formula (I), (IA), or (IB), when $R^2$ is $C_1$-$C_3$ haloalkyl, $R^6$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, when $R^2$ is $C_2$ haloalkyl, $R^6$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In a certain embodiment, when $R^2$ is $C_1$-$C_3$ haloalkyl, $R^6$ is selected from $C_1$-$C_3$ alkyl optionally substituted with one or more substituents independently selected from halogen, —$OR^{10}$, —$SR^{10}$, —N($R^{10}$)$_2$, —NO$_2$, =O, and —CN. In certain embodiments, when $R^2$ is $C_1$-$C_3$ haloalkyl, $R^6$ is methyl, ethyl or propyl, each of which is substituted with at least one halogen. In certain embodiments, when $R^2$ is $C_1$-$C_3$ haloalkyl, $R^6$ is —CH$_2$CF$_3$. In a certain embodiment, when $R^2$ is $C_1$-$C_3$ haloalkyl, $R^6$ is methyl, ethyl or propyl, each of which is optionally substituted with at least one halogen. In certain embodiments, when $R^2$ is $C_1$-$C_3$ haloalkyl, $R^6$ is unsubstituted methyl, ethyl or propyl. In certain embodiments, when $R^2$ is $C_1$-$C_3$ haloalkyl, $R^6$ is methyl. In certain embodiments, when $R^2$ is $C_1$-$C_3$ haloalkyl, $R^6$ is ethyl. In certain embodiments, when $R^2$ is $C_1$-$C_3$ haloalkyl, $R^6$ is propyl.

In certain embodiments for a compound of Formula (I), (IA), or (IB), when $R^2$ is $C_3$ cycloalkyl, $R^6$ is selected from $C_1$-$C_3$ alkyl substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, when $R^2$ is $C_3$ cycloalkyl, $R^6$ is $C_2$ alkyl substituted with one or more substituents independently selected from halogen, —$OR^{10}$, —$SR^{10}$, —(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN.

In certain embodiments, when $R^2$ is $C_3$ cycloalkyl, $R^6$ is selected from $C_1$-$C_3$ alkyl substituted with one or more substituents independently selected from halogen, —$OR^{10}$, —$SR^{10}$, —N($R^{10}$)$_2$, —NO$_2$, =O, and —CN. In certain embodiments, when $R^2$ is $C_3$ cycloalkyl, $R^6$ is methyl, ethyl or propyl, each of which is substituted with at least one halogen. In certain embodiments, when $R^2$ is $C_3$ cycloalkyl, $R^6$ is —CH$_2$CF$_3$.

In certain embodiments for a compound of Formula (I), (IA), or (IB), when $R^2$ is optionally substituted $C_4$-$C_5$ cycloalkyl, $R^6$ is selected from $C_1$-$C_3$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, when $R^2$ is optionally substituted $C_4$-$C_5$ cycloalkyl, $R^6$ is selected from $C_2$ alkyl optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, $R^6$ is methyl, ethyl or propyl, each of which is substituted with at least one halogen. In certain embodiments, $R^6$ is methyl, ethyl or propyl, each of which is optionally substituted with at least one halogen. In certain embodiments, $R^6$ is —CH$_2$CF$_3$. In certain embodiments, $R^6$ is —CH$_2$CH$_3$.

In certain embodiments for a compound of Formula (I), (IA), or (IB), $R^7$ is $C_1$-$C_3$ alkyl which is optionally substituted with one or more substituents independently selected from halogen —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In certain embodiments, $R^7$ is selected from $C_1$-$C_3$ alkyl optionally substituted with one or more substituents independently selected from halogen, —$OR^{10}$, —N($R^{10}$)$_2$, —NO$_2$, =O, =S, and —CN. In certain embodiments, $R^7$ is unsubstituted $C_1$-$C_3$ alkyl. In certain embodiments, $R^7$ is methyl, ethyl or propyl. In certain embodiments, $R^7$ is methyl.

In certain embodiments, the compound of Formula (I) is represented by Formula (IC):

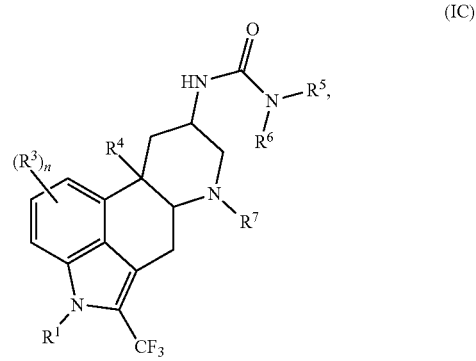

(IC)

or a salt thereof.

In certain embodiments, the compound of Formula (I) is represented by Formula (ID):

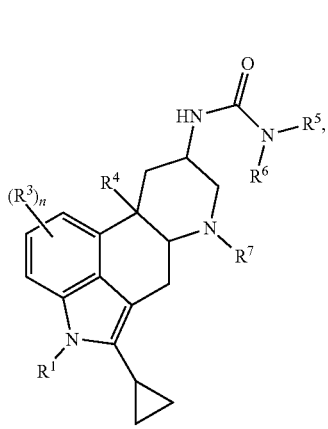

(ID)

or a salt thereof.

In certain embodiments, the compound is represented by:

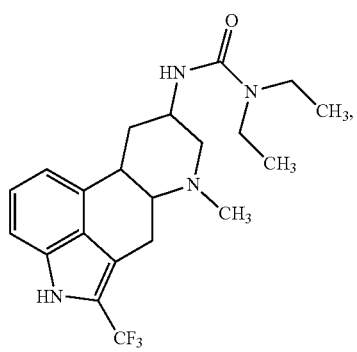

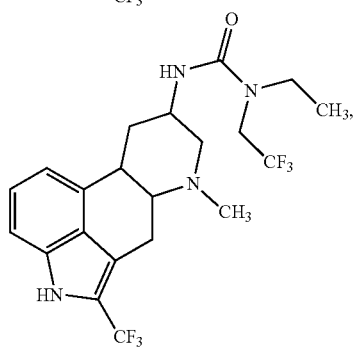

or a salt of any one thereof.

In certain embodiments, the compound is represented by:

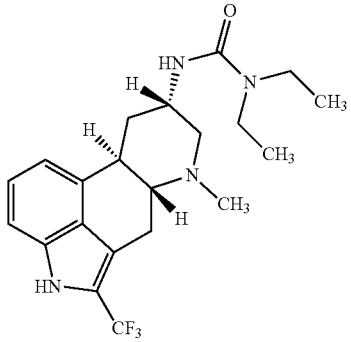 [SMILES: CCN(CC)C(=O)N[C@H]1C[C@@H]2c3cccc4[nH]c(C(F)(F)F)c(c34)C[C@H]2N(C)C1]

or a salt thereof.

In certain embodiments, the compound is represented by:

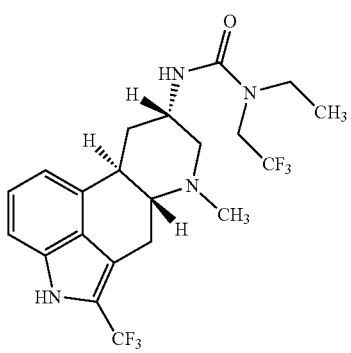 [SMILES: CCN(CC(F)(F)F)C(=O)N[C@H]1C[C@@H]2c3cccc4[nH]c(C(F)(F)F)c(c34)C[C@H]2N(C)C1]

or a salt thereof.

In certain embodiments, the compound is represented by:

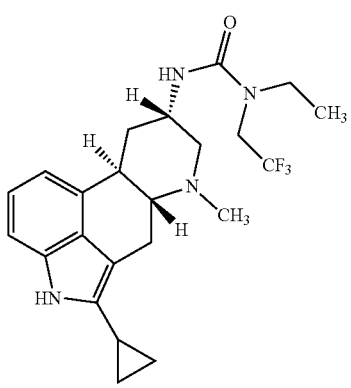 [SMILES: CCN(CC(F)(F)F)C(=O)N[C@H]1C[C@@H]2c3cccc4[nH]c(C5CC5)c(c34)C[C@H]2N(C)C1]

or a salt thereof.

In certain embodiments, for a compound or salt of Formula (IA): $R^1$ is selected from hydrogen; and $C_1$-$C_3$ alkyl, optionally substituted with one or more substituents independently selected from halogen, —$OR^{10}$, —$NO_2$, and —CN; $R^2$ is $C_1$ haloalkyl; $R^3$ is selected from halogen, $C_1$-$C_3$ alkyl, $C_1$-$C_3$ haloalkyl, —$OR^{10}$, —$NO_2$, and —CN; $R^4$ is hydrogen, —OH or —$OCH_3$; $R^5$ is selected from $C_1$-$C_3$ alkyl optionally substituted with one or more substituents independently selected from halogen, —$OR^{10}$, —$N(R^{10})_2$, —$NO_2$, and —CN, such as $R^5$ is unsubstituted $C_1$-$C_3$ alkyl; $R^6$ is selected from $C_1$-$C_3$ alkyl optionally substituted with one or more substituents independently selected from halogen, —$OR^{10}$, —$N(R^{10})_2$, —$NO_2$, and —CN, such as $R^6$ is unsubstituted $C_1$-$C_3$ alkyl or $C_1$-$C_3$ alkyl substituted with one or more halogens, e.g., $R^6$ is $CH_2CF_3$; $R^7$ is selected from methyl optionally substituted with one or more substituents independently selected from halogen, —$OR^{10}$, and —CN, e.g., $R^7$ is unsubstituted methyl; $R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, and 2, e.g., n is 0.

In certain embodiments, for a compound or salt of Formula (IA): $R^1$ is hydrogen; $R^2$ is $C_1$ haloalkyl; $R^3$ is selected from halogen, $C_1$-$C_3$ alkyl, $C_1$-$C_3$ haloalkyl, —$OR^{10}$, —$NO_2$, and —CN; $R^4$ is hydrogen; $R^5$ is selected from $C_1$-$C_3$ alkyl optionally substituted with one or more substituents independently selected from halogen, —$OR^{10}$, —$N(R^{10})_2$, —$NO_2$, and —CN, such as $R^5$ is unsubstituted ethyl; $R^6$ is selected from $C_1$-$C_3$ alkyl optionally substituted with one or more substituents independently selected from halogen, —$OR^{10}$, —$N(R^{10})_2$, —$NO_2$, and —CN, such as $R^6$ is ethyl or $CH_2CF_3$; $R^7$ is selected from methyl optionally substituted with one or more substituents independently selected from halogen, —$OR^{10}$, and —CN, e.g., $R^7$ is unsubstituted methyl; $R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, and 2, e.g., n is 0.

In certain embodiments, for a compound of Formula (IA): $R^1$ is selected from hydrogen; and $C_1$-$C_3$ alkyl optionally substituted with one or more substituents independently selected from halogen, —$OR^{10}$, —$NO_2$, and —CN; $R^2$ is $C_3$-$C_5$ cycloalkyl optionally substituted with one or more substituents independently selected from halogen, —$OR^{10}$, —$N(R^{10})_2$, —$C(O)OR^{10}$, —$OC(O)R^{10}$, —$NO_2$, =O, =S, =$N(R^{10})$, and —CN, e.g., $R^2$ is unsubstituted $C_3$-$C_5$ cycloalkyl; $R^3$ is selected from halogen, $C_1$-$C_3$ alkyl, $C_1$-$C_3$ haloalkyl, —$OR^{10}$, —$NO_2$, and —CN; $R^4$ is hydrogen, —OH or —$OCH_3$; $R^5$ is selected from $C_1$-$C_3$ alkyl optionally substituted with one or more substituents independently selected from halogen, —$OR^{10}$, —$N(R^{10})_2$, —$NO_2$, and —CN, such as $R^5$ is unsubstituted $C_1$-$C_3$ alkyl; $R^6$ is selected from $C_1$-$C_3$ alkyl substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN; e.g., $R^6$ is $CH_2CF_3$; $R^7$ is selected from methyl optionally substituted with one or more substituents independently selected from halogen, —$OR^{10}$, and —CN, e.g., $R^7$ is unsubstituted methyl; $R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, and 2, e.g., n is 0.

In certain embodiments, for a compound of Formula (IA): $R^1$ is selected from hydrogen; $R^2$ is $C_3$ cycloalkyl optionally substituted with one or more substituents independently selected from halogen, —$OR^{10}$, —$N(R^{10})_2$, —$C(O)OR^{10}$, —$OC(O)R^{10}$, —$NO_2$, =O, =S, =$N(R^{10})$, and —CN, e.g., $R^2$ is unsubstituted cyclopropyl; $R^3$ is selected from halogen, $C_1$-$C_3$ alkyl, $C_1$-$C_3$ haloalkyl, —$OR^{10}$, —$NO_2$, and —CN; $R^4$ is hydrogen, —OH or —$OCH_3$; $R^5$ is selected from $C_1$-$C_3$ alkyl optionally substituted with one or more substituents independently selected from halogen, —$OR^{10}$, —$N(R^{10})_2$, —$NO_2$, and —CN, such as $R^5$ is unsubstituted $C_1$-$C_3$ alkyl; $R^6$ is selected from $C_1$-$C_3$ alkyl substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN; e.g., $R^6$ is $CH_2CF_3$; $R^7$ is selected from methyl optionally substituted with one or more substituents independently selected from halogen, —$OR^{10}$, and —CN, e.g., $R^7$ is unsubstituted methyl; $R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and n is selected from 0, 1, and 2, e.g., n is 0.

One aspect of the present invention provides a compound selected from the group consisting of the following:

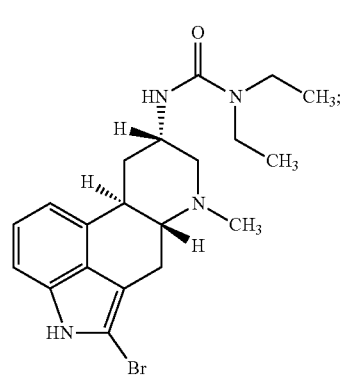

A8H

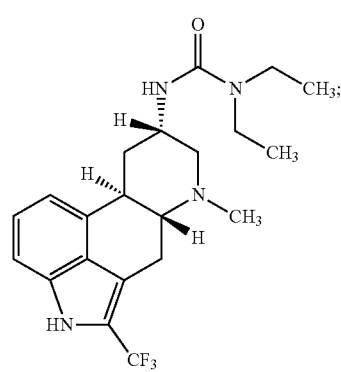

A9H

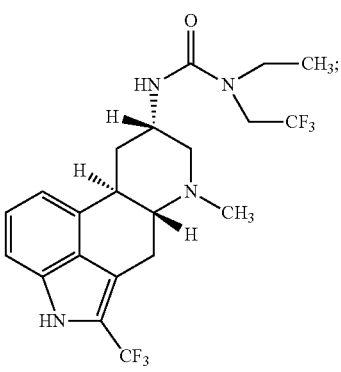

A16H

-continued

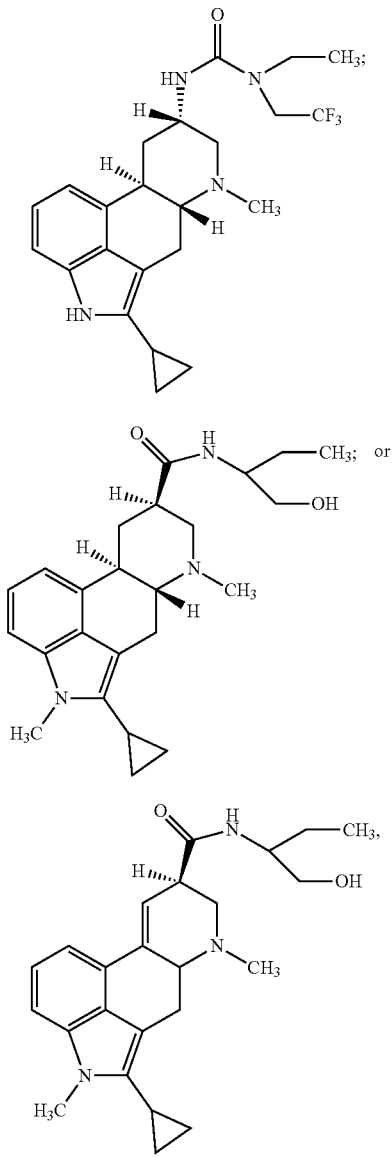

or a pharmaceutically acceptable salt or prodrug thereof.

Another aspect of the present invention provides a compound having the following structure:

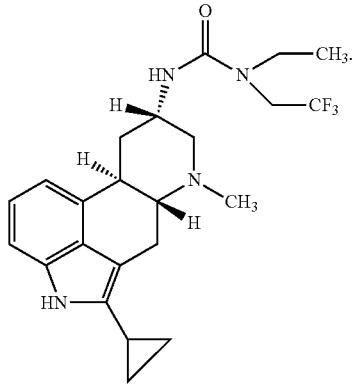

A17H

Still other aspects of the present invention provides a compound having the following structure:

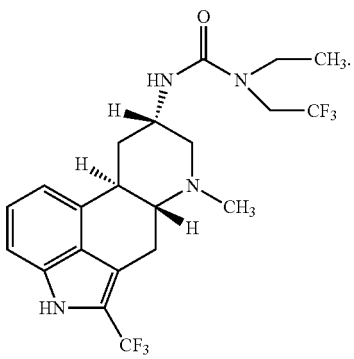

A16H

In yet another example, the present invention provides a compound having following structure:

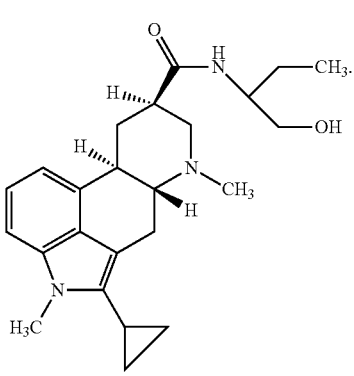

D13H

In yet another example, the present invention provides a compound having following structure:

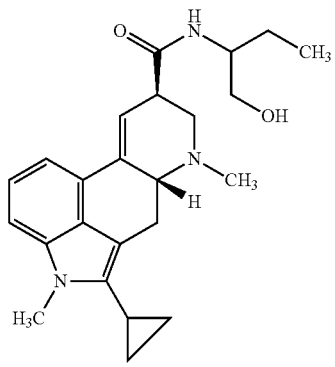

D13-i

Processes

In one aspect, the present disclosure provides a process for preparing a compound represented by the formula:

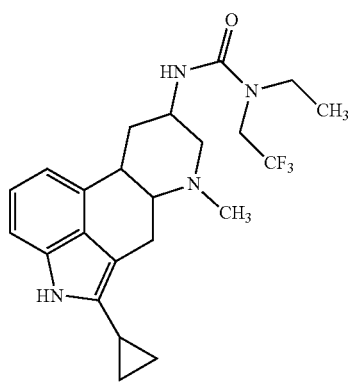 [SMILES: CCN(CC(F)(F)F)C(=O)NC1CC2c3cccc4[nH]c(C5CC5)c(c34)CC2N(C)C1]

comprising contacting a compound of formula 5:

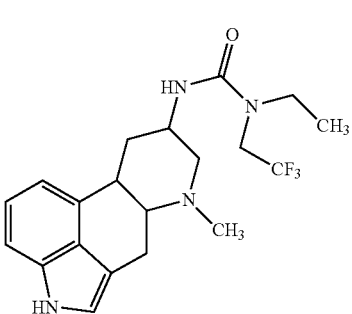

with a brominating agent under suitable halogenation conditions.

In one aspect, the present disclosure a process for preparing a compound of formula 5:

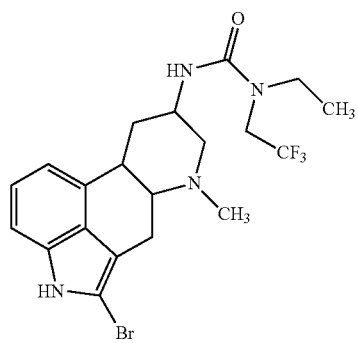

with cyclopropyl boronic acid under cross-coupling conditions.

In one aspect, the present disclosure provides a process for preparing a compound of Formula 6:

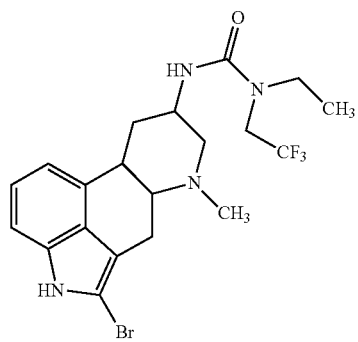

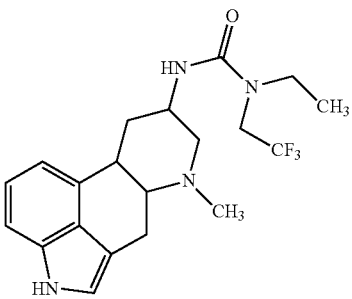

comprising contacting a compound of formula 4:

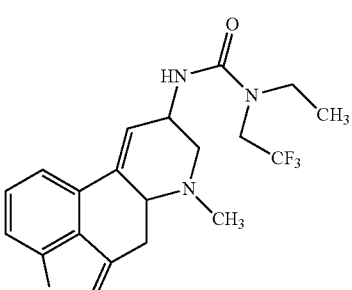

with $H_2$ under suitable hydrogenation conditions.

In one aspect, the present disclosure provides a process for preparing a compound of formula 4:

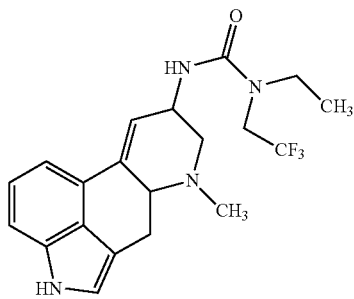

comprising contacting a compound of formula 3:

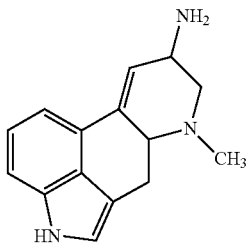

with ethyl(2,2,2-trifluoroethyl)amine and triphosgene under suitable conditions to form a urea derivative.

Another embodiment of the present invention provides a process for preparing compound A17H:

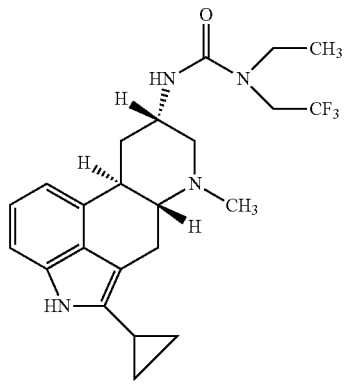

comprising reacting a compound of formula 6:

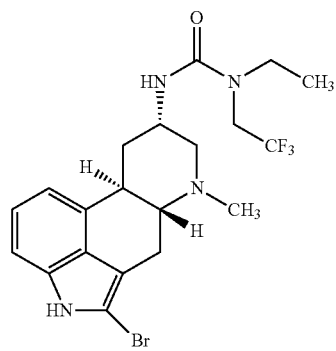

with a coupling group under suitable cross-coupling conditions.

In some embodiments, the coupling group is a cyclopropylboronic acid. In one embodiment, the suitable cross-coupling conditions are described in Example 4, step 4 below.

Yet another aspect of the present invention provides a process for preparing a compound of formula 6:

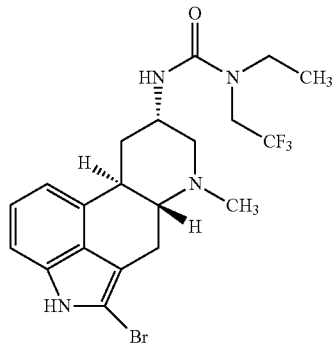

by reacting the compound of formula 5:

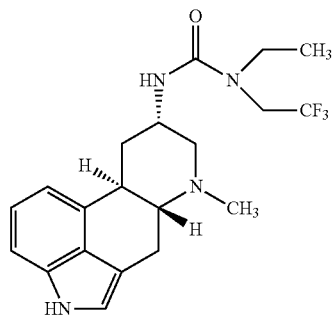

with a brominating agent under suitable halogenation conditions.

In some embodiments, the brominating agent is bromotrimethylsilane. In one embodiment, the suitable halogenation conditions are described in Example 4, step 3 below.

Still another embodiment of the present invention provides a process for preparing a compound of formula 5:

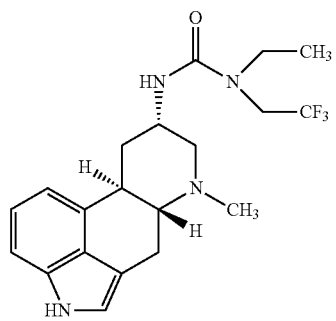

by reacting a compound of formula 4:

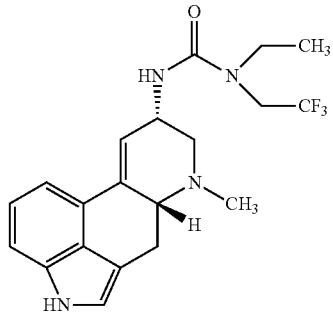

4 with H$_2$ under suitable hydrogenation conditions.

In one embodiment, suitable hydrogenation conditions are described in Example 4, step 2 below.

Another embodiment of the present invention provides a process for preparing a compound of formula 4

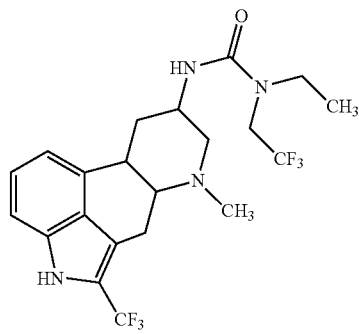 [SMILES: CCN(CC(F)(F)F)C(=O)NC1CC2c3cccc4[nH]c(C(F)(F)F)c(c34)CC2N(C)C1]

5 comprising contacting a compound of formula 5:

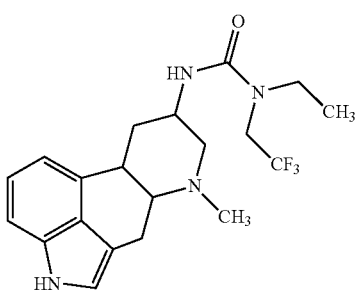

5 with a trifluoromethylation reagent under suitable trifluoromethylation conditions.

Yet another embodiment of the present invention provides a process for preparing a compound of formula A16H:

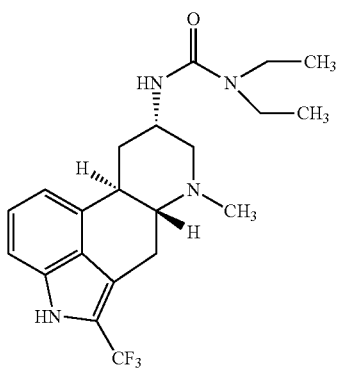

A16H

4 by reacting a compound of formula 3:

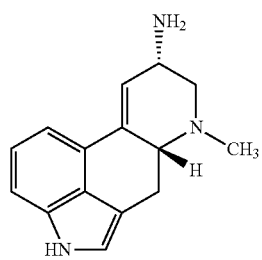

3 comprising reacting a compound of formula 5

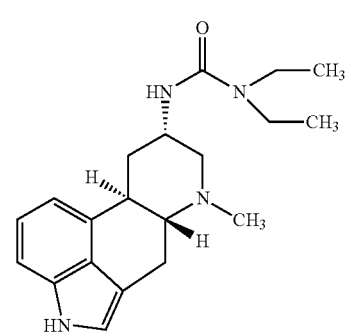

5 with ethyl(2,2,2-trifluoroethyl)amine under suitable conditions to form a urea derivative.

In one embodiment, suitable conditions for forming a urea derivative are described in Example 4, step 1 below.

In one aspect, the present disclosure provides a process for preparing a compound of the formula:

with a trifluoromethylation agent under suitable trifluoromethylation conditions.

In some embodiments, the trifluoromethylation agent is Togni's reagent I(3,3-dimethyl-1(trifluoromethyl)-1,2-benziodooxole). In one embodiment, the suitable trifluoromethylation conditions are described in Example 3, step 3 below.

Another embodiment of the present invention provides a process for preparing a compound of formula D13H:

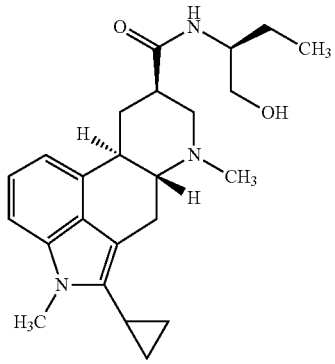

D13H comprising reacting a compound of formula 10:

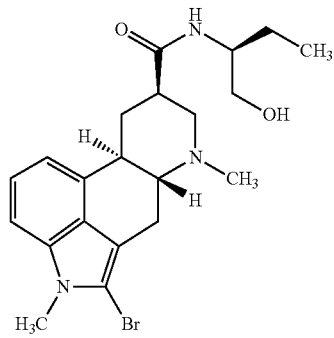

10 with a coupling group under suitable cross-coupling conditions.

In one embodiment the suitable cross-coupling conditions are described in Example 6, step 3 below.

Yet another embodiment of the present invention provides a process for preparing a compound of formula 10:

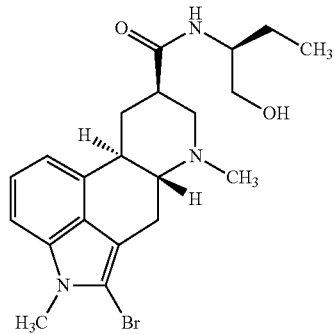

10 by reacting a compound of formula 9:

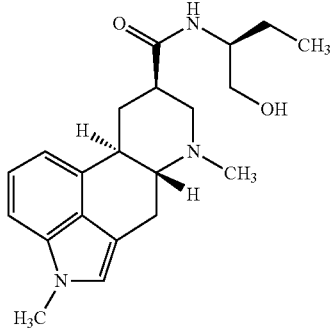

9 with a brominating agent under suitable halogenation conditions.

In one embodiment, the suitable halogenation conditions are described in Example 6, step 2 below.

Another embodiment of the present invention provides a process for preparing a compound of formula 9:

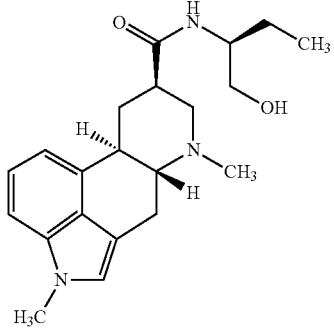

9 by reacting a compound of formula 7:

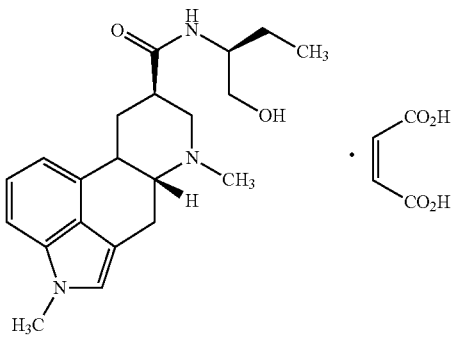

7 with $H_2$ under suitable hydrogenation conditions.

In one embodiment, the suitable hydrogenation conditions are described in Example 6, Step 1 below.

Pharmaceutically Acceptable Salts, Solvates, Clathrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+$ ($C_{1-4}$alkyl)$_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates), clathrates, and cocrystals. The term solvate includes hydrates (e.g., hemihydrate, monohydrate, dihydrate, trihydrate, tetrahydrate, and the like). It should be understood that any compound of this invention may exist in crystalline or amorphous forms or mixtures thereof.

In addition to the compounds described herein, pharmaceutically acceptable derivatives or prodrugs of these compounds may also be employed in compositions to treat or prevent the herein identified disorders. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

Pharmaceutical Compositions

In one aspect, the present disclosure provides pharmaceutically acceptable compositions that comprise any of the compounds or salts as described herein, and optionally comprise a pharmaceutically acceptable carrier, adjuvant or vehicle. In one aspect, the present disclosure provides a pharmaceutical composition comprising a compound or salt described herein and a pharmaceutically acceptable excipient.

The pharmaceutically acceptable carriers, adjuvants, and vehicles are well-known in the art. As used herein, they include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disorder being treated. In certain embodiments, the compounds of the invention may be administered orally or parenterally at dosage levels of about 0.0001 mg/kg to about 70 mg/kg, of subject body weight per day, one or more times a day, to obtain the desired therapeutic effect. Alternatively, the dosing schedule of the compounds of the present invention may vary.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectable forms, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

When formulated for nasal administration, the absorption across the nasal mucous membrane may be further enhanced by surfactants, such as, for example, glycocholic acid, cholic acid, taurocholic acid, ethocholic acid, deoxycholic acid, chenodeoxycholic acid, dehdryocholic acid, glycodeoxycholic acid, cycledextrins and the like in an amount in the range of between about 0.1 and 15 weight percent, between about 0.5 and 4 weight percent, or about 2 weight percent. An additional class of absorption enhancers reported to exhibit greater efficacy with decreased irritation is the class of alkyl maltosides, such as tetradecylmaltoside (Arnold, J J et al., 2004, J Pharm Sci 93: 2205-13; Ahsan, F et al., 2001, Pharm Res 18:1742-46), all of which are hereby incorporated by reference.

In human therapeutics, the physician will determine the dosage regimen that is most appropriate according to a preventive or curative treatment and according to the age, weight, stage of the disease and other factors specific to the subject to be treated. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, or about 1000 mg, and in some embodiments from about 10 mg to about 500 mg of the active ingredient or a combination of essential ingredients per dosage unit form.

The amount of active ingredient in the formulation, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Methods of Use of the Compounds and Compositions

The disclosure provides methods of treating or preventing diseases or disorders by administering a compound or salt of any one of Formulas (I), (IA), (IB), (IC), (ID), or (IE), or a pharmaceutical composition thereof, to a subject in need thereof. The disclosure provides compounds with receptor agonism or antagonism profiles for a variety of receptors. Compounds that modulate these receptors have been described for treating diseases such as a symptom of Parkinson's Disease, restless leg syndrome, migraine, postpartum hemorrhage, senile dementia, diabetic reset, hyperprolactinaemia, or cardiovascular disease (see S. Hisahara et al., Dopamine receptors and Parkinson's Disease, Int. J. Med. Chem., v 2011, 1-16 (2011); N. Visanji et al., Dopamine D3 receptor stimulation underlies the development of L-DOPA-induced dyskinesia in animal models of Parkinson's Disease, Neurobiology of Disease, v. 35, 184-192 (2009); P. Goadsby et al., Pathophysiology of migraine: A disorder of sensory processing, Physiol Rev, v. 97, 553-622 (2017); P. Raskin et al., Bromocriptine-QR therapy for the management of type 2 diabetes mellitus: developmental basis and therapeutic profile summary, Expert Rev Endocrinol Metab., v. 11, n. 2, 113-148 (2016); J. Verhelst et al., Hyperprolactinemia: pathophysiology and management, Treatments in Endocrinology, 23-32 (2003); and J. Unterscheider et al., Standard Medical Therapy for Postpartum Hemorrhage, Ch. 43, 355-360; H. Liu, et al., Ergot alkaloids: synthetic approaches to lysergic acid and clavinet alkaloids, Nat Prod Rep. (2017); the contents of each of which are incorporated by reference herein).

A compound or salt of any one of Formulas (I), (IA), (IB), (IC), (ID), or (IE), or a pharmaceutical composition thereof, may be administered to a subject for preventing or treating ALS, Alzheimer's disease, extra-pyramidal disorders, depression, nausea, emesis, insomnia, aggression, Huntington's disease, cardiopulmonary disease, fibrogenesis, pulmonary arterial hypertension, anxiety, drug addictions, dystonia, parasomnia.

In certain embodiments, the compounds and salts of the disclosure are used for preventing diseases or disorders, such as preventing migraines. In certain embodiments, the compounds and salts of the disclosure are used for treating a symptom of Parkinson's Disease. In certain embodiments, the compounds and salts of the disclosure are used for treating or preventing a cardiovascular disorder. In practicing the methods, therapeutically effective amounts of the compounds, salts or compositions, described herein, supra, are administered.

The disclosure provides methods for antagonizing receptors including 5-HT$_{2B}$ receptors, adrenergic alpha$_{1A}$receptors and D$_{2L}$ and D$_3$ receptors using the compounds, salts and compositions, described herein. In practicing the methods, therapeutically effective amounts of the compounds, salts or compositions, described herein, supra, are administered.

Also provided are methods for agonizing the 5-HT$_{1D}$, 5-HT$_{1A}$ and D$_{2L}$ receptors using the compounds, salts and compositions described herein. In some embodiments, methods of selectively agonizing the 5-HT$_{1D}$ receptor over the 5-HT$_{1B}$ receptor using the compounds, salts and compositions described herein are provided.

Strong agonism of the 5-HT$_{1B}$ receptor frequently leads to adverse cardiovascular effects due to excessive vasoconstriction. While selective agonism is preferred, antagonism of adrenergic receptors such as, for example, alpha$_{1A}$, alpha$_{1D}$, alpha$_{2A}$, alpha$_{2B}$ and alpha$_{2C}$ by migraine therapeutics can reduce such vasoconstriction caused by strong 5-HT$_{1B}$ agonism. In some embodiments, the compounds, salts and compositions selectively agonizes the 5-HT$_{1D}$ receptor over the 5-HT$_{1B}$ receptor and antagonize one or more of adrenergic alpha$_{1A}$ receptor, adrenergic alpha$_{2A}$ receptor, or adrenergic alpha$_{2B}$ receptor. In other embodiments, the compounds, salts and compositions agonizes one or more of 5-HT$_{1B}$ or 5-HT$_{1D}$ receptor and antagonize one or more of adrenergic alpha$_{1A}$ receptor, adrenergic alpha$_{2A}$ receptor, or adrenergic alpha$_{2B}$ receptor.

Moreover, strong agonism of the 5-HT$_{2B}$ receptor frequently leads to undesirable cardiovascular complications such as valvular heart disease. Accordingly, selective agonism where the 5-HT$_{2B}$ is not activated is highly desirable.

In some embodiments, it is desirable to select compounds or salts that are useful for the treatment of one or more symptoms of Parkinson's disease. An ideal compound or salt for such treatment should have selective agonist activities for the dopaminergic D$_2$ receptor. Additionally, in some embodiments, it may be advantageous for a compound or salt to have weak to moderate 5-HT$_{1A}$, and 5-HT$_{1A}$, receptor agonist activities. In other embodiments, it may be advantageous for a compound to have 5-HT$_{2A}$ receptors antagonism activities.

In one aspect, the present disclosure provides a method of treating a disease or disorder, comprising administering a compound represented by Formula (IE):

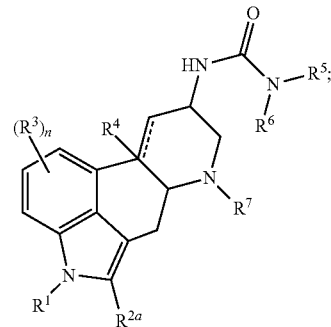

(IE)

or a salt thereof, to a subject in need thereof, wherein:
====== represents an optional double bond;
R$^1$ is selected from hydrogen; and C$_1$-C$_3$ alkyl, C$_3$-C$_5$ cycloalkyl, C$_{2-4}$ alkenyl, C$_3$-C$_5$ cycloalkenyl, C$_{2-4}$ alkynyl, each of which is optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)OR$^{10}$, —OC(O)R$^{10}$, —NO$_2$, =O, =S, =N(R$^{10}$), and —CN;
R$^{2a}$ is selected from halogen, C$_1$-C$_3$ haloalkyl and C$_3$-C$_5$ cycloalkyl, wherein C$_3$-C$_5$ cycloalkyl is optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;
R$^3$ is selected from halogen, C$_1$-C$_3$ alkyl, C$_1$-C$_3$ haloalkyl, —OR$^{10}$, —N(R$^{10}$)$_2$, —C(O)R$^{10}$, —C(O)OR$^{10}$, —OC(O)R$^{10}$, —NO$_2$, and —CN;
R$^4$ is absent or selected from hydrogen and OR$^{10}$, wherein R$^4$ is absent when ====== is a double bond and R$^4$ is selected from hydrogen and OR$^{10}$ when ====== is a single bond;
R$^5$ is selected from C$_1$-C$_3$ alkyl optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN, wherein when R$^2$ is selected from C$_1$ haloalkyl and ====== is a double bond, R$^5$ is C$_1$-C$_3$ alkyl optionally substituted with one or more substituents independently selected from —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;
R$^6$ is selected from C$_1$-C$_3$ alkyl optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN, wherein when R$^2$ is C$_3$ cycloalkyl, R$^6$ is selected from substituted C$_1$-C$_3$ alkyl;
R$^7$ is selected from C$_1$-C$_3$ alkyl, C$_{2-4}$ alkenyl, and C$_{2-4}$ alkynyl, each of which is optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;
R$^{10}$ is independently selected at each occurrence from hydrogen; and C$_1$-C$_3$ alkyl optionally substituted with one or more substituents independently selected from halogen, —OH, —OCH$_3$, —CF$_3$, —SH, —NH$_2$, —NO$_2$, and —CN; and
n is selected from 0, 1, 2, and 3.

In certain embodiments, for a compound of Formula (IE), $R^{2a}$ is selected from halogen, e.g., Br. The compound of Formula (IE) may be represented by:

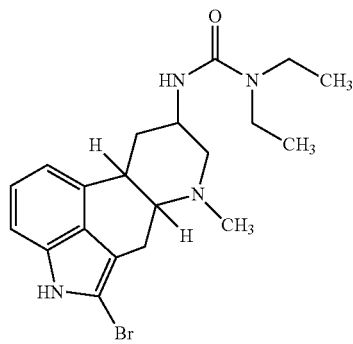 [SMILES: CCN(CC)C(=O)NC1CC2c3cccc4[nH]c(Br)c(c34)CC2N(C)C1]

or a salt thereof. The compound of Formula (IE) may be represented by:

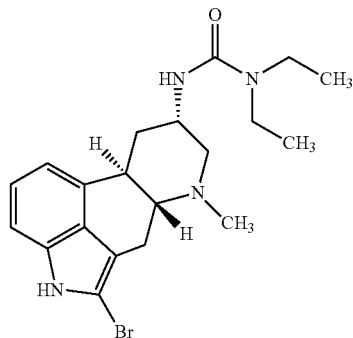 [SMILES: CCN(CC)C(=O)N[C@H]1C[C@@H]2c3cccc4[nH]c(Br)c(c34)C[C@H]2N(C)C1]

or a salt thereof.

A compound or salt or pharmaceutical compositions of the disclosure may be used for the manufacture of a medicament for treating migraines, Parkinson's disease, and/or cardiovascular disease. Other embodiments provide a compound according to the present invention for use in the treatment of migraines, Parkinson's disease, and/or cardiovascular disease.

In one aspect, the present disclosure provides the use of a compound or salt described herein or a pharmaceutical composition described herein for the manufacture of a medicament for the treatment of a disease or disorder. In one aspect, the present disclosure provides the use of a compound or salt described herein or a pharmaceutical composition described herein for the manufacture of a medicament for the treatment of a Parkinson's Disease, restless leg syndrome, migraine, postpartum hemorrhage, senile dementia, diabetic reset, hyperprolactinaemia, or cardiovascular disease.

In other embodiments, compound A16H is an antagonist for the Adrenergic $\alpha_{1A}$; Dopamine $D_{2L}$ & $D_3$; and Serotonin 5-$HT_{1B}$, 5-$HT_{1D}$, 5-$HT_{2A}$, 5-$HT_{2B}$, and 5-$HT_7$ receptors.

In another embodiment, compound A17H is an agonist for the Dopamine $D_{2L}$ & $D_3$ receptors. In still other embodiments A17H is an antagonist for the Adrenergic $\alpha_{1A}$; Dopamine $D_{2L}$ & $D_3$; and Serotonin 5-$HT_{1A}$, 5-$HT_{1D}$, 5-$HT_{2A}$, 5-$HT_{2B}$, and 5-$HT_7$ receptors. In some embodiments, compounds A16H and A17H are useful for treating cardiovascular disease.

In yet another embodiment, compound D13H is an agonist for the Dopamine $D_{2L}$ & $D_3$ and Serotonin 5-$HT_{1B}$, 5-$HT_{1D}$, 5-$HT_{1F}$, and 5-$HT_7$ receptors. In still other embodiments, compound D13H is an antagonist for the Dopamine $D_3$ and Serotonin 5-$HT_{2A}$, 5-$HT_{2B}$, and 5-$HT_7$ receptors. In some embodiments, compound D13H is useful for treating migraines and/or Parkinson's disease.

Still other embodiments provide a method of treating migraine in a subject comprising administering to the subject a therapeutically effective amount of a compound of the present invention. Other embodiments of the present invention provide a method of agonizing the Serotonin 5-$HT_{1D}$ receptor in a subject comprising administering to the subject a therapeutically effective amount of a compound of the present invention. In some embodiments the subject is administered a therapeutically effective amount of compound D13H.

Other embodiments of the present invention provides a method of treating one or more symptoms of Parkinson's disease in a subject comprising administering to the subject a therapeutically effective amount of a compound of the present invention. Still other embodiments provides a method of agonizing the Dopamine $D_{2L}$ and $D_3$ receptors in a subject comprising administering to the subject a therapeutically effective amount of a compound of the present invention. In some embodiments, the subject is administered a therapeutically effective amount of compound D13H.

Yet another aspect of the present invention provides a method of treating one or more symptoms of cardiovascular disease in a subject comprising administering to the subject a therapeutically effective amount of a compound of the present invention. In other embodiments the subject is administered a therapeutically effective amount of compound A16H or A17H.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, management, prevention, or amelioration of one or more symptoms associated with migraine, Parkinson's disease, cardiovascular disease.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the compounds and compositions provided herein may be used with other agents to agonize and or antagonize the receptors mentioned above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

EXAMPLES

All commercially available solvents and reagents were used as received. Proton nuclear magnetic resonance spectra were recorded on a Bruker Avance II 300 MHz instrument.

For the calibration of spectra, solvent-peak and tetramethylsilane signals were used. Spectra were recorded at room temperature. Purity analyses of the samples were performed either on a Waters 2695 HPLC/Waters ZQ MS system (Waters Corporation, Milford, Mass.) or on an Agilent HPLC/Waters ZQ MS system (Agilent Technologies, Santa Clara, Calif.). Compound purification was carried out on a Hanbon Preparative HPLC system (Jiangsu Hanbon Science & Technology, LTD., Huai'An City, Jiangsu, China). Unless otherwise indicated, the HPLC methods utilized are as described below:

HPLC Method A: Agilent HPLC
 Column: Phenomenex Kinetex EVO C18, 5 μM, 4, 6×50 mm
  Column temp: 35° C.
  Sample temp: 35° C.
  Detection: UV 220 nM
  Sample Diluent: MeCN
  Flow Rate: 1.3 mL/min
  Injection: 3-5 μL
  Analysis time: 5 min
  In Neutral Conditions
  Mobil Phase A: MeCN:$H_2O$=5:95 with 20 mM $NH_4HCO_2$ buffer, pH=7.4
  Mobil Phase B: MeCN:$H_2O$=80:20 with 20 mM $NH_4HCO_2$ buffer, pH=7.4
  Gradient: adjusted according to the compound properties.

HPLC Method B: Waters 2695 HPLC
 Column: Phenomenex Kinetex EVO C18, 5 μM, 4, 6×50 mm
  Column temp: 25° C.
  Sample temp: 25° C.
  Detection: UV 220 nM
  Sample Diluent: MeCN
  Flow Rate: 1.3 or 2.0 mL/min
  Injection: 1-3 μL
  Analysis time: 2 or 5 min
  In Neutral Conditions
  Mobil Phase A: MeCN:$H_2O$=5:95 with 20 mM $NH_4HCO_2$ buffer, pH=7.4
  Mobil Phase B: MeCN:$H_2O$=80:20 with 20 mM $NH_4HCO_2$ buffer, pH=7.4
  In Acidic Conditions
  Mobil Phase A: Aqueous 0.05% v/v TFA
  Mobil Phase B: MeCN 0.05% v/v TFA
  Gradient: adjusted according to the compound properties HPLC Method C: Harbon Preparative HPLC
 Column: Phenomenex AXIA Gemini NX 5 μM, 30×100 mm
  Column temp: 25° C.
  Sample temp: 25° C.
  Detection: UV 220 nM
  Sample Diluent: MeCN
  Flow Rate: 40 mL/min
  Injection: 1000-30004
  Analysis time: 10 or 14 min
  In Neutral Conditions
  Mobil Phase A: MeCN:$H_2O$=5:95 with 20 mM $NH_4HCO_2$ buffer, pH=7.4
  Mobil Phase B: MeCN:$H_2O$=80:20 with 20 mM $NH_4HCO_2$ buffer, pH=7.4
  In Acidic Conditions
  Mobil Phase A: Aqueous 0.05% v/v TFA
  Mobil Phase B: MeCN 0.05% v/v TFA
  In Basic Conditions
  Mobil Phase A: MeCN:$H_2O$=5:95 with 20 mM $NH_4HCO_2$ buffer, pH=8.0
  Mobil Phase B: MeCN:$H_2O$=80:20 with 20 mM $NH_4HCO_2$ buffer, pH=8.0
  Gradient: adjusted according to the compound properties.

Scheme 1:

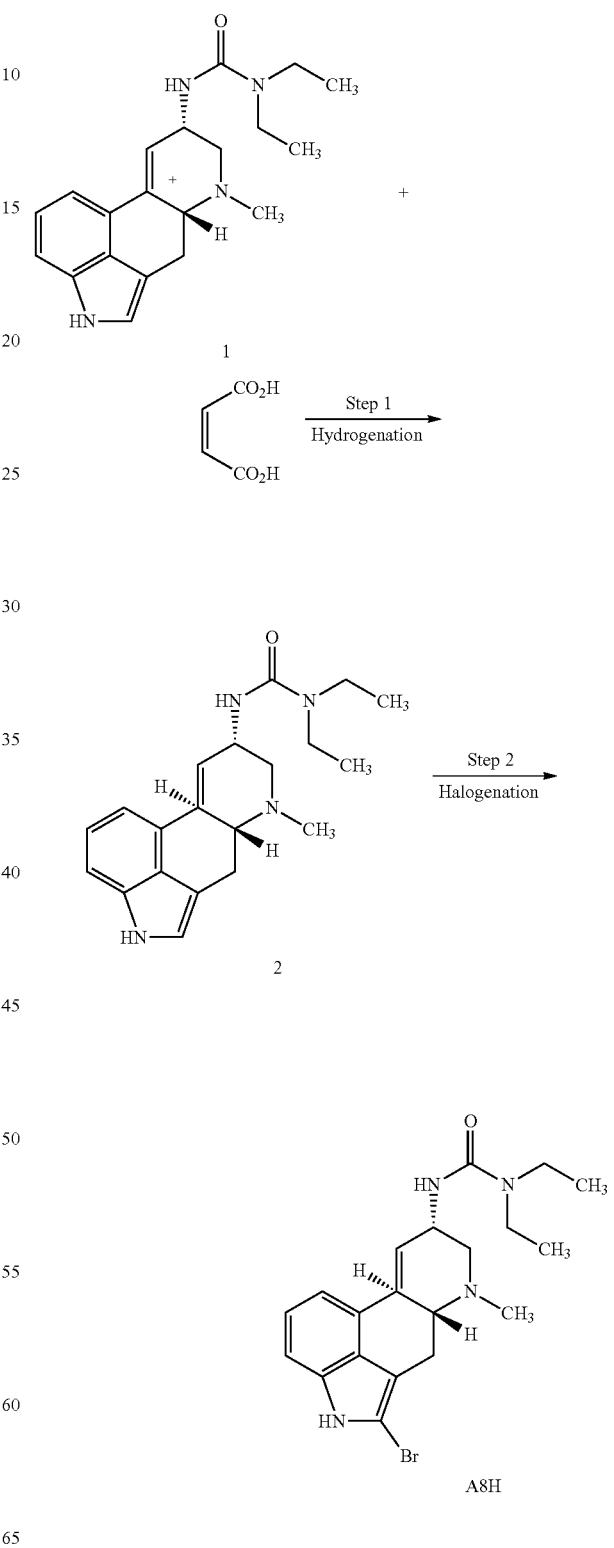

Example 1: Synthesis of 3-((6aR,9S, 10aR)-5-bromo-7-methyl-4,6,6a,7,8,9,10,10a-octahydroindolo[4,3-fg]quinolin-9-yl)-1,1-diethylurea (Compound A8H)

Step 1: 1,1-diethyl-3-((6aR,9S,10aR)-7-methyl-4, 6, 6a, 7, 8, 9, 10, 10a-octahydroindolo[4,3-fg]quinolin-9-yl)urea

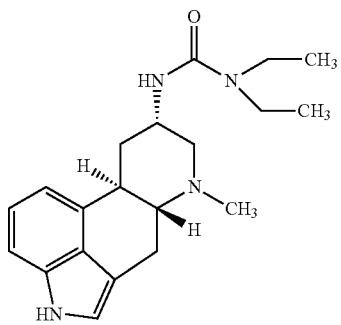

2

Lisuride maleate 1 (200 mg, 0.44 mmol) was dissolved in MeOH (10 mL/mmol) and Pd/C (0.3 equiv) was added. The reaction mixture was stirred under hydrogen atmosphere (5 bar) in a stainless steel autoclave at room temperature overnight. The reaction mixture was filtered through a pad of Celite™, washed with MeOH (3 Å~5 mL/mmol) and DCM (3 Å~5 mL/mmol), then the filtrate was concentrated. The crude product was purified by preparative HPLC to give compound 2 (43 mg, 29% yield). APCI MS, m/z 341 [M+H]$_+$, HPLC-MS (220 nm) 98% (AUC). $^1$H-NMR (300 MHz, DMSO-d$_6$): δ 1.04 (6H, t, J=6.9 Hz); 1.40-1.54 (1H, m); 1.95-2.06 (1H, m); 2.34 (4H, s); 2.54-2.64 (2H, m); 2.85 (1H, d, J=11.8 Hz); 3.1-3.3 (5H, m); 4.0 (1H, s); 5.55 (1H, d, J=7.45 Hz); 6.7 (1H, d, J=6.9 Hz); 6.91-7.04 (2H, m); 7.07-7.16 (1H, m); 10.62 (1H, s).

Step 2: 3-((6aR,9S, 10aR)-5-bromo-7-methyl-4,6, 6a,7,8,9,10,10a-octahydroindolo[4,3-fg]quinolin-9-yl)-1,1-diethylurea

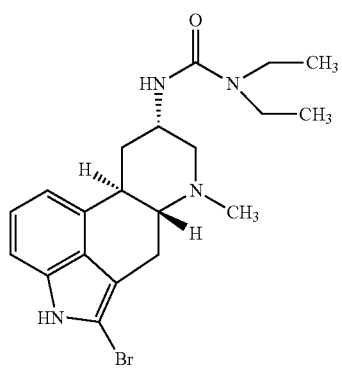

A8H

Bromotrimethylsilane (6 equiv) was dissolved in dry DMSO (20 mL/mmol) and the solution was stirred at rt. for 15 min. Compound 2 (100 mg, 0.29 mmol) (1 equiv) was added and the mixture was stirred at room temperature for 10 min. The mixture was poured into ice-water (100 mL/mmol) and the pH was adjusted to 8-9 with aq. ammonia and extracted with DCM (3 Å~20 mL/mmol). The combined organic phase was washed with aq. Na$_2$S$_2$O$_3$ (2 Å~10 mL/mmol) and brine (2 Å~10 mL/mmol) then dried over MgSO$_4$, filtered and concentrated. The crude product was purified by flash chromatography (DCM:MeOH, 0-10%) to give compound A8H (5.8 mg, 14% yield). APCI MS, m/z 419 [M+H]$_+$, HPLC-MS (220 nm) 93% (AUC). $^1$H-NMR (300 MHz, DMSO-d$_6$): δ 1.04 (6H, t, J=7 Hz); 1.41-1.54 (1H, m); 1.96-2.07 (1H, m); 2.36 (3H, s); 2.40-2.48 (2H, m); 2.53-2.62 (1H, m); 2.86 (1H, d, J=11.8 Hz); 2.92-3.04 (1H, m); 3.06-3.3 (5H, m); 3.97-4.05 (1H, m); 5.56 (1H, d, J=7.57 Hz); 6.75 (1H, d, J=6.7 Hz); 6.98-7.1 (2H, m); 11.38 (1H, s).

Scheme 2:

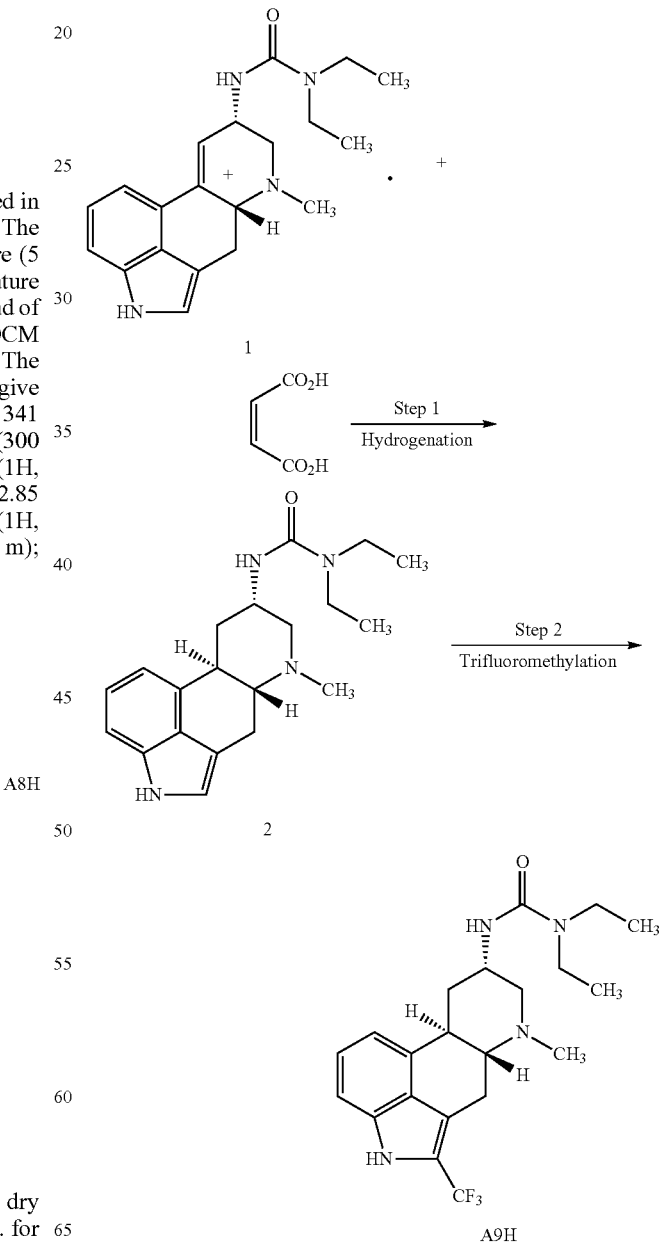

Example 2: Synthesis of 1,1-diethyl-3-((6aR,9S,10aR)-7-methyl-5-(trifluoromethyl)-4,6,6a,7,8,9,10,10a-octahydroindolo[4,3-fg]quinolin-9-yl)urea (Compound A9H)

Step 1: 1,1-diethyl-3-((6aR,9S,10aR)-7-methyl-4,6,6a,7,8,9,10,10a-octahydroindolo[4,3-fg]quinolin-9-yl)urea

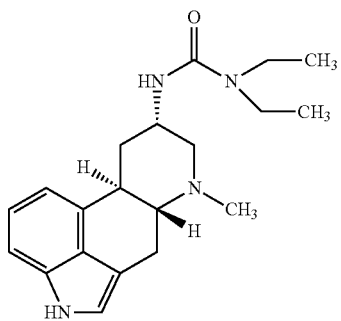

2

Lisuride maleate 1 (200 mg, 0.44 mmol) was dissolved in MeOH (10 mL/mmol) and Pd/C (0.3 equiv) was added. The reaction mixture was stirred under hydrogen atmosphere (5 bar) in a stainless steel autoclave at room temperature overnight. The reaction mixture was filtered through a pad of Celite™, washed with MeOH (3 Å~5 mL/mmol) and DCM (3 Å~5 mL/mmol), then the filtrate was concentrated. The crude product was purified by preparative HPLC to give compound 2 (43 mg, 29% yield). APCI MS, m/z 341 [M+H]+, HPLC-MS (220 nm) 98% (AUC). ¹H-NMR (300 MHz, DMSO-d₆): δ 1.04 (6H, t, J=6.9 Hz); 1.40-1.54 (1H, m); 1.95-2.06 (1H, m); 2.34 (4H, s); 2.54-2.64 (2H, m); 2.85 (1H, d, J=11.8 Hz); 3.1-3.3 (5H, m); 4.0 (1H, s); 5.55 (1H, d, J=7.45 Hz); 6.7 (1H, d, J=6.9 Hz); 6.91-7.04 (2H, m); 7.07-7.16 (1H, m); 10.62 (1H, s).

Step 2: 1,1-diethyl-3-((6aR,9S,10aR)-7-methyl-5-(trifluoromethyl)-4,6,6a,7,8,9,10,10a-octahydroindolo[4,3-fg]quinolin-9-yl)urea (Compound A9H)

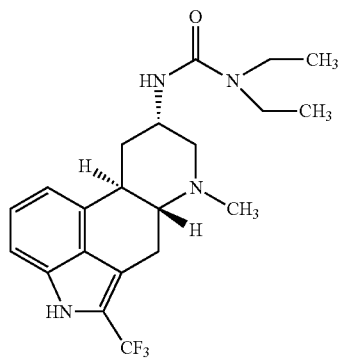

A9H

Copper (II) acetate (0.2 equiv) and Togni's reagent (1.2 equiv) were dissolved in MeOH (17 mL/mmol) under Argon and Compound 2 (100 mg, 0.29 mmol) was added at room temperature. The reaction mixture was heated at 40° C. for 90 min, then it was cooled to room temperature, treated with sat. Na₂CO₃ solution and extracted with DCM (3 Å~10 mL/mmol). The organic phase was dried over MgSO₄, filtered and concentrated. The crude product was purified by flash chromatography (DCM:MeOH, 0-10%) to give compound A9H (47 mg, 39% yield). APCI MS, m/z 409 [M+H]+, HPLC-MS (220 nm) 90% (AUC). ¹H-NMR (300 MHz, DMSO-d₆): δ 1.04 (6H, t, J=7.1 Hz); 1.43-1.58 (1H, m); 2.02-2.16 (1H, m); 2.36 (4H, s); 2.55-2.75 (1H, m); 2.86 (1H, d, J=11.2 Hz); 2.98-3.01 (1H, m); 3.11-3.29 (4H, m); 3.36-3.45 (1H, m); 3.97-4.06 (1H, m); 5.56 (1H, d, J=7.4 Hz); 6.81-6.9 (1H, m); 7.17-7.27 (2H, m); 11.76 (1H, s).

Scheme 3:

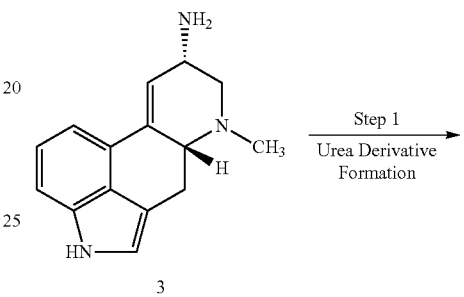

3

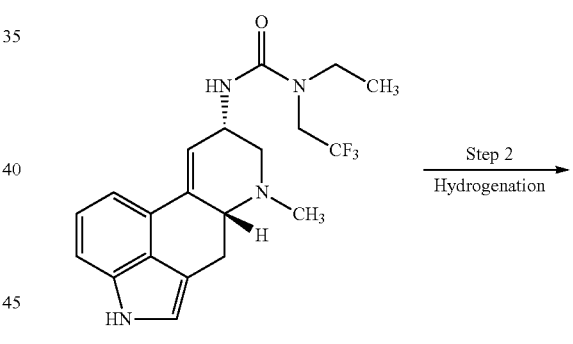

4

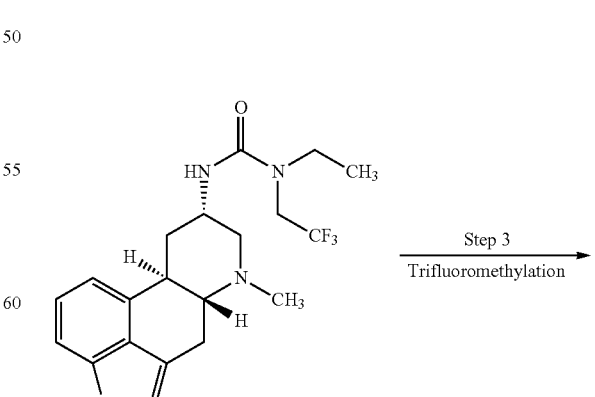

5

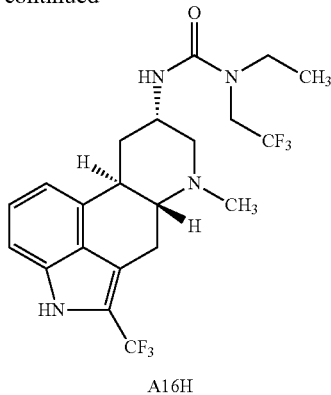

A16H

Example 3: Synthesis of 1-ethyl-3-((6aR,9S,10aR)-7-methyl-5-(trifluoromethyl)-4,6,6a,7,8,9,10,10aoctahydroindolo[4,3-fg]quinolin-9-yl)-1-(2,2,2-trifluoroethyl)urea (Compound A16H)

Step 1: 1-ethyl-3-((6aR,9S)-7-methyl-4,6,6a,7,8,9-hexahydroindolo[4,3-fg]quinolin-9-yl)-1-(2,2,2-trifluoroethyl)urea

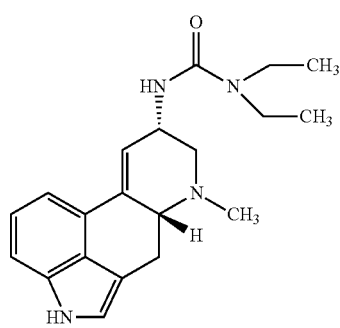

4

A solution of triphosgene (0.75 equiv) and ethyl(2,2,2-trifluoroethyl)amine (1.5 equiv) in dry DCM (5 mL/mmol) under Argon was stirred at 0° C. for 15 min then allowed to warm to room temperature. TEA (4.5 equiv) was added and stirred at room temperature for 1 h, then a solution of 8-aminoergoline 3 (200 mg, 0.84 mmol (1 equiv.)) in a 1:1 mixture of dry DCM and dry THF (10 mL/mmol) was added and stirred at rt for 20 h. The reaction mixture was diluted with 5% aq. K₂CO₃ (5 mL/mmol), and extracted with DCM (3 Å~3 mL/mmol). The combined organic phase was concentrated and the crude product was purified by flash chromatography (DCM:MeOH, 0-10%) to give compound 4 (169 mg, 51% yield). APCI MS, m/z 393 [M+H]+, HPLCMS (220 nm)>99% (AUC).

Step 2: 1-ethyl-3-((6aR,9S,10aR)-7-methyl-4,6,6a,7,8,9,10,10a-octahydroindolo[4,3-fg]quinolin-9-yl)-1-(2,2,2-trifluoroethyl)urea

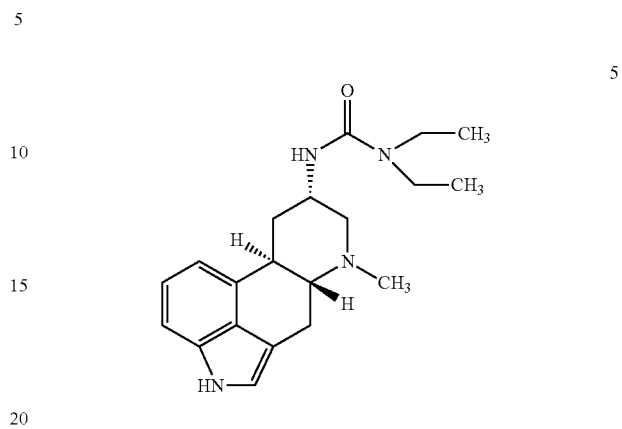

5

Compound 4 (167 mg, 0.43 mmol) was dissolved in 1,4-dioxane (25 mL/mmol). Raney nickel (12 equiv) was added, then the mixture was stirred under hydrogen atmosphere (5 bar) in a stainless steel autoclave at 70° C. for 14 h. The reaction mixture was filtered through a pad of Celite™, washed with MeOH (3 Å~5 mL/mmol) and DCM (3 Å~5 mL/mmol), then the filtrate was concentrated. The crude product was dissolved in DCM (6 mL/mmol) and washed with 1M aq. NaHCO₃ (2 Å~3 mL/mmol) and with water (2 Å~3 mL/mmol). The combined organic phase was dried over MgSO₄, filtered and concentrated. The crude product was purified by flash chromatography (DCM:MeOH, 0-10%) to give compound 5 (65 mg, 38.7% yield). APCI MS, m/z 395 [M+H]+, HPLC-MS (220 nm) 99% (AUC). $^1$H-NMR (300 MHz, DMSO-d₆): δ 1.09 (3H, t, J=6.95 Hz); 1.43-1.6 (1H, m); 1.95-2.1 (1H, m); 2.35 (3H, s); 2.55-2.66 (2H, m); 2.81-3.12 (2H, m); 3.36-3.68 (3H, m); 3.96-4.14 (2H, m); 4.15-4.27 (1H, m); 5.91-6.06 (1H, m); 6.66-6.78 (1H, m); 6.94-7.2 (3H, m),10.63 (1H, s).

Step 3: 1-ethyl-3-((6aR,9S,10aR)-7-methyl-5-(trifluoromethyl)-4,6,6a,7,8,9,10,10a-octahydroindolo[4,3-fg]quinolin-9-yl)-1-(2,2,2-trifluoroethyl)urea (Compound A16H)

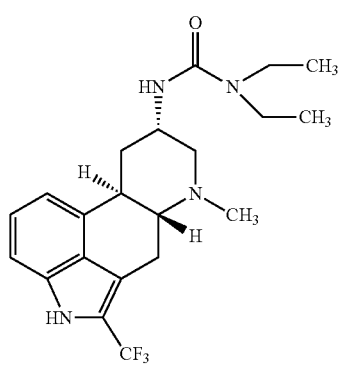

A16H

Copper (II) acetate (0.2 equiv) and Togni's reagent (1.2 equiv) were dissolved in MeOH (17 mL/mmol) under Ar and compound 5 (55 mg, 0.14 mmol) was added at room temperature. The reaction mixture was heated at 40° C. for 90 min, then it was cooled to room temperature, treated with sat. Na$_2$CO$_3$ solution and extracted with DCM (3 Å~10 mL/mmol). The organic phase was dried over MgSO$_4$, filtered and concentrated. The crude product was purified by flash chromatography (DCM:MeOH, 0-10%) to give compound A16H (16 mg, 25% yield). APCI MS, m/z 463 [M+H]$_+$, HPLC-MS (220 nm) 90% (AUC). $^1$H-NMR (300 MHz, DMSO-d$_6$): δ 1.08 (3H, t, J=6.9 Hz); 1.46-1.59 (1H, m); 2.04-2.16 (1H, m); 2.34 (3H, s); 2.36-2.4 (1H, m); 2.54-2.69 (2H, m); 2.89 (1H, d, J=11.7 Hz); 3.01-3.14 (1H, m); 3.33-3.46 (3H, m); 3.97-4.2 (3H, m); 6.0 (1H, d, J=7.2 Hz); 6.8-6.87 (1H, m); 7.16-7.26 (2H, m), 11.76 (1H, s).

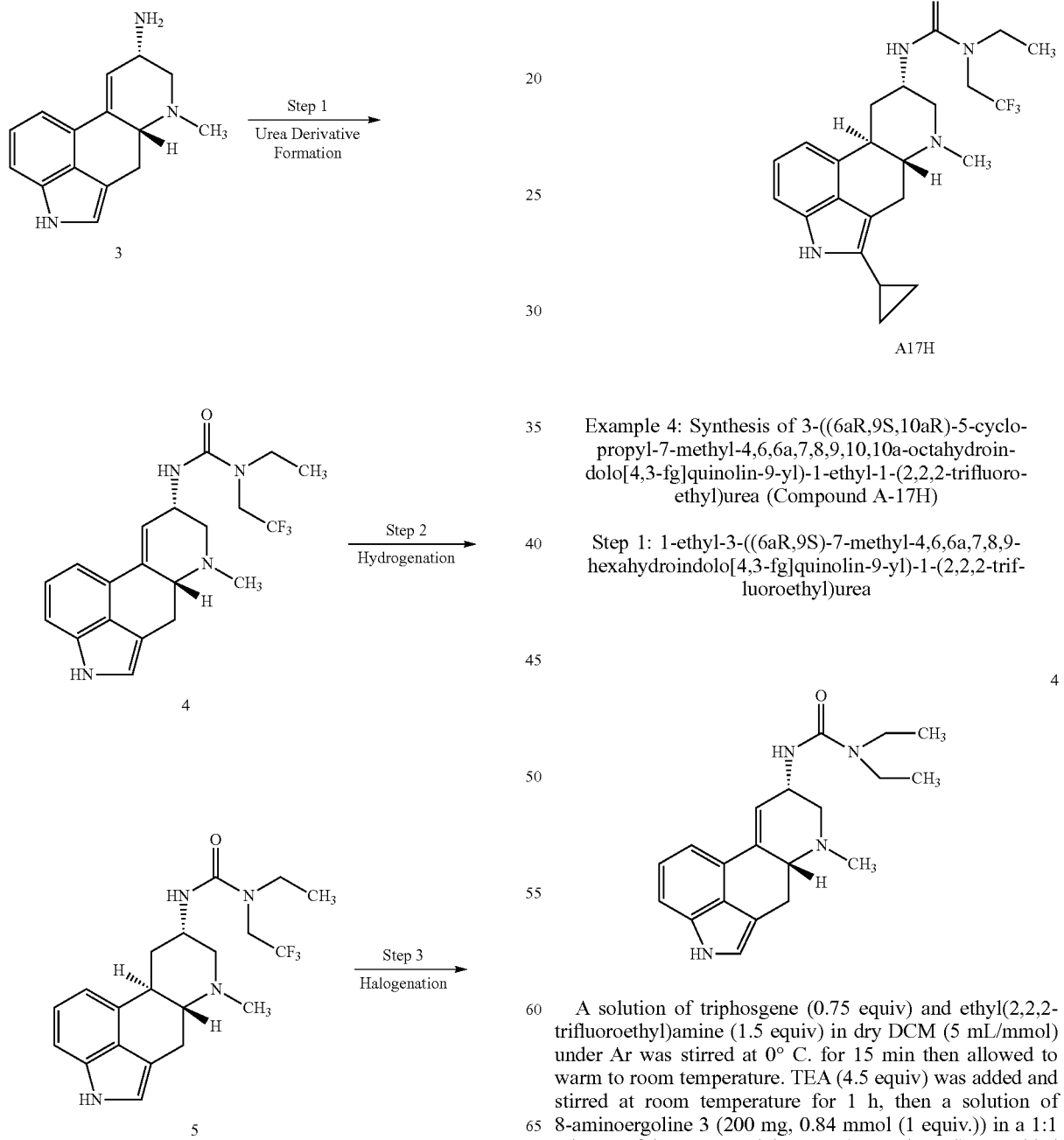

Example 4: Synthesis of 3-((6aR,9S,10aR)-5-cyclopropyl-7-methyl-4,6,6a,7,8,9,10,10a-octahydroindolo[4,3-fg]quinolin-9-yl)-1-ethyl-1-(2,2,2-trifluoroethyl)urea (Compound A-17H)

Step 1: 1-ethyl-3-((6aR,9S)-7-methyl-4,6,6a,7,8,9-hexahydroindolo[4,3-fg]quinolin-9-yl)-1-(2,2,2-trifluoroethyl)urea A solution of triphosgene (0.75 equiv) and ethyl(2,2,2-trifluoroethyl)amine (1.5 equiv) in dry DCM (5 mL/mmol) under Ar was stirred at 0° C. for 15 min then allowed to warm to room temperature. TEA (4.5 equiv) was added and stirred at room temperature for 1 h, then a solution of 8-aminoergoline 3 (200 mg, 0.84 mmol (1 equiv.)) in a 1:1 mixture of dry DCM and dry THF (10 mL/mmol.) was added and stirred at rt for 20 h. The reaction mixture was diluted with 5% aq. K$_2$CO$_3$ (5 mL/mmol), and extracted with DCM (3 Å~3 mL/mmol). The combined organic phase was concentrated and the crude product was purified by flash chromatography (DCM:MeOH, 0-10%) to give compound 4 (169 mg, 51% yield). APCI MS, m/z 393 [M+H]$_+$, HPLCMS (220 nm)>99% (AUC).

Step 2: 1-ethyl-3-((6aR,9S,10aR)-7-methyl-4,6,6a,7,8,9,10,10a-octahydroindolo[4,3-fg]quinolin-9-yl)-1-(2,2,2-trifluoroethyl)urea

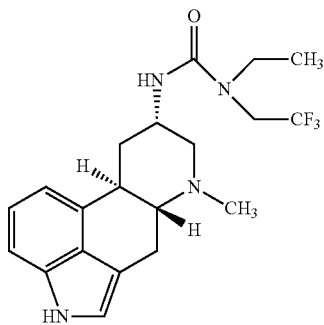

5

Compound 4 (167 mg, 0.43 mmol) was dissolved in 1,4-dioxane (25 mL/mmol). Raney nickel (12 equiv) was added, then the mixture was stirred under hydrogen atmosphere (5 bar) in a stainless steel autoclave at 70° C. for 14 h. The reaction mixture was filtered through a pad of Celite™, washed with MeOH (3 Å~5 mL/mmol) and DCM (3 Å~5 mL/mmol), then the filtrate was concentrated. The crude product was dissolved in DCM (6 mL/mmol) and washed with 1M aq. NaHCO$_3$ (2 Å~3 mL/mmol) and with water (2 Å~3 mL/mmol). The combined organic phase was dried over MgSO$_4$, filtered and concentrated. The crude product was purified by flash chromatography (DCM:MeOH, 0-10%) to give compound 5 (65 mg, 38.7% yield). APCI MS, m/z 395 [M+H]$_+$, HPLC-MS (220 nm) 99% (AUC). $^1$H-NMR (300 MHz, DMSO-d$_6$): δ 1.09 (3H, t, J=6.95 Hz); 1.43-1.6 (1H, m); 1.95-2.1 (1H, m); 2.35 (3H, s); 2.55-2.66 (2H, m); 2.81-3.12 (2H, m); 3.36-3.68 (3H, m); 3.96-4.14 (2H, m); 4.15-4.27 (1H, m); 5.91-6.06 (1H, m); 6.66-6.78 (1H, m); 6.94-7.2 (3H, m),10.63 (1H, s).

Step 3: 3-((6aR,9S,10aR)-5-bromo-7-methyl-4,6,6a,7,8,9,10,10aoctahydroindolo[4,3-fg]quinolin-9-yl)-1-ethyl-1-(2,2,2-trifluoroethyl)urea

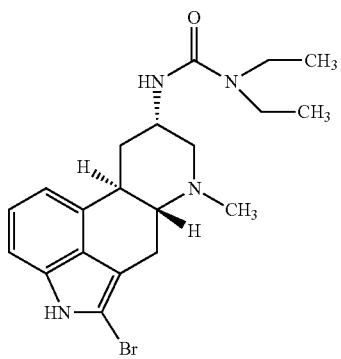

6

Bromotrimethylsilane (6 equiv) was dissolved in dry DMSO (20 mL/mmol) and the solution was stirred at rt. for 15 min. Compound 5 (224 mg, 0.54 mmol (1 equiv)) was added and the mixture was stirred at room temperature for 10 min. The mixture was poured into ice-water (100 mL/mmol) and the pH was adjusted to 8-9 with aq. ammonia and extracted with DCM (3 Å~20 mL/mmol). The combined organic phase was washed with aq. Na$_2$S$_2$O$_3$ (2 Å~10 mL/mmol) and brine (2 Å~10 mL/mmol) then dried over MgSO$_4$, filtered and concentrated. The crude product was purified by flash chromatography (DCM:MeOH, 0-10%) to give compound 6 (239 mg, 89% yield). APCI MS, m/z 473 [M+H]$_+$, HPLC-MS (220 nm) 92% (AUC).

Step 4: 3-((6aR,9S,10aR)-5-cyclopropyl-7-methyl-4,6,6a,7,8,9,10,10aoctahydroindolo[4,3-fg]quinolin-9-yl)-1-ethyl-1-(2,2,2-trifluoroethyl)urea (Compound A17H)

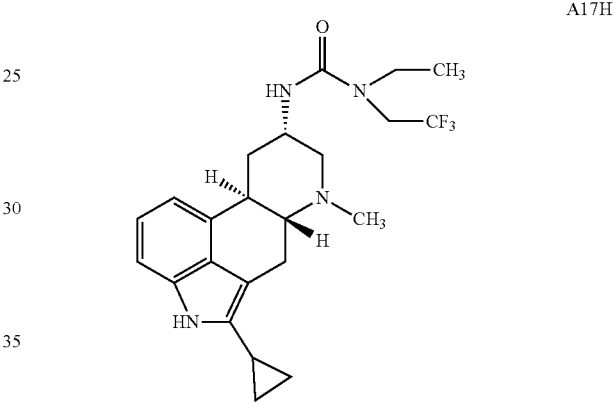

A17H

A mixture of 1,2-dimethoxyethane (6 mL/mmol) and water (1.5 mL/mmol) was flushed with argon and a mixture of compound 6 (235 mg, 0.50 mmol), cyclopropylboronic acid (1.5 equiv) and K$_3$PO$_4$ (3.7 equiv) were added to it. The mixture was flushed with argon for 10 min and then Pd(dppf)Cl$_2$ (0.01 equiv) was added, and the resulting mixture was stirred at 90° C. overnight. Then the mixture was cooled to room temperature and diluted with EtOAc (2 mL/mmol) and water (2 mL/mmol). The mixture was filtered and then the layers were separated. The organic phase was washed with brine (10 mL/mmol) then dried over MgSO$_4$, filtered and concentrated. The crude product was purified by preparative HPLC to give compound A17H (32 mg, 15% yield). APCI MS, m/z 435 [M+H]$_+$, HPLC-MS (220 nm) 93% (AUC). $^1$H-NMR (300 MHz, DMSO-d$_6$): δ 0.74-0.87 (2H, m); 0.87-0.97 (2H, m); 1.09 (3H, t, J=7.2 Hz); 1.41-1.54 (1H, m); 1.93-2.07 (2H, m); 2.29-2.45 (4H, m); 2.53-2.63 (1H, m); 2.83-3.04 (2H, m); 3.24-3.29 (1H, m); 3.33-3.46 (2H, m); 3.95-4.22 (3H, m); 5.97 (1H, d, J=7.2 Hz); 6.63 (1H, d, J=6.9 Hz); 6.84-7.0 (2H, m), 10.24 (1H, s).

Scheme 5:

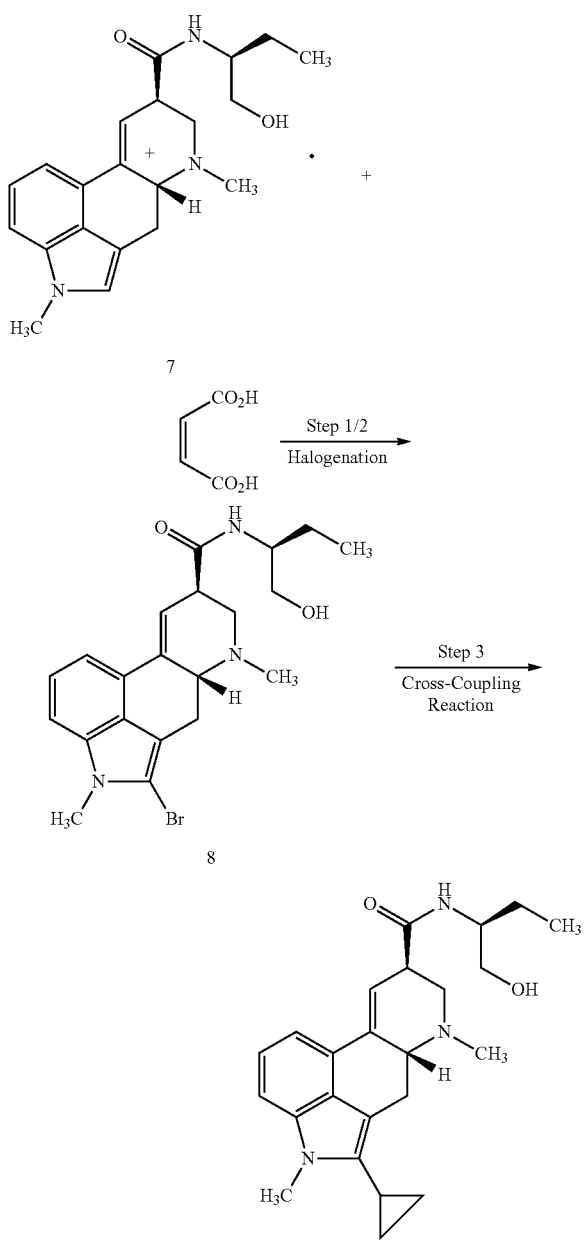

Example 5: Synthesis of (6aR,9R)-5-cyclopropyl-N—((S)-1-hydroxybutan-2-yl)-4,7-dimethyl-4,6,6a,7,8,9-hexahydroindolo[4,3-fg]quinoline-9-carboxamide (Compound D13)

Step 1: Methysergide Base

Methysergide maleate 7 was dissolved in DCM (2 mL/mmol) and washed with 10% NaHCO$_3$ (2 Å~2 mL/mmol). The organic phase was dried over MgSO$_4$, filtered and concentrated under vacuum to give the methysergide base 7a.

Step 2: (6aR,9R)-5-bromo-N—((S)-1-hydroxybutan-2-yl)-4,7-dimethyl-4,6,6a,7,8,9-hexahydroindolo[4,3-fg]quinoline-9-carboxamide

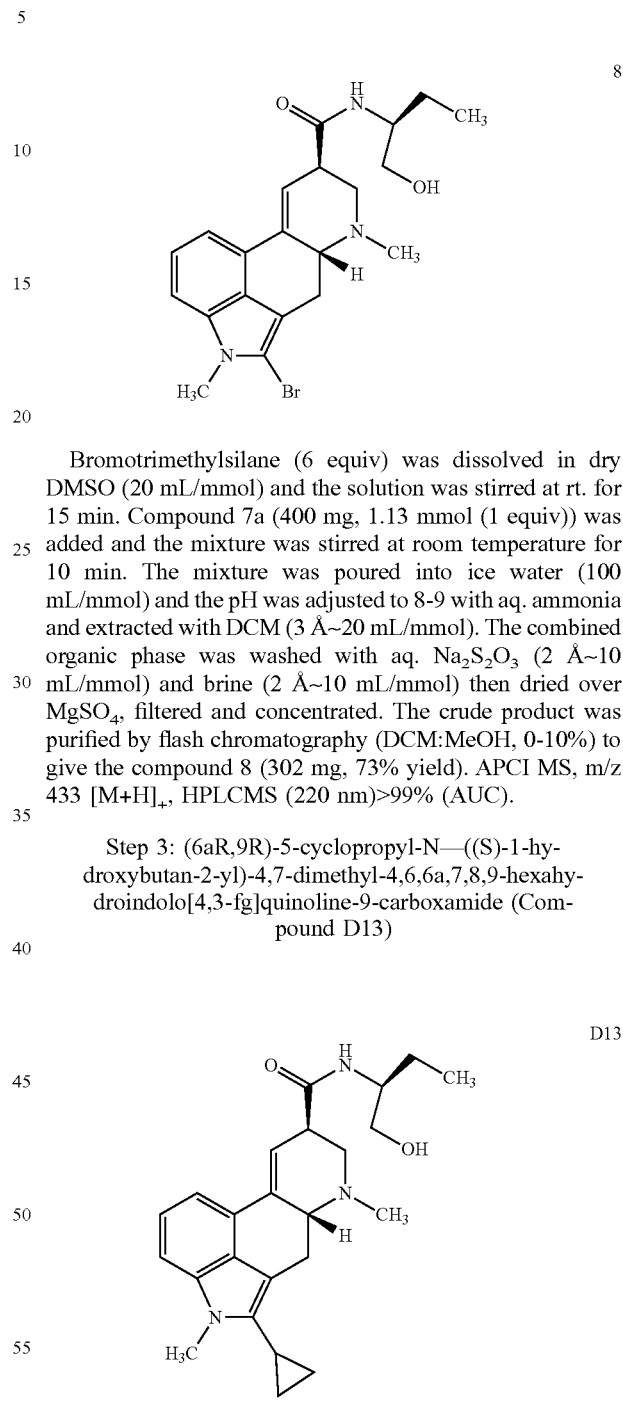

Bromotrimethylsilane (6 equiv) was dissolved in dry DMSO (20 mL/mmol) and the solution was stirred at rt. for 15 min. Compound 7a (400 mg, 1.13 mmol (1 equiv)) was added and the mixture was stirred at room temperature for 10 min. The mixture was poured into ice water (100 mL/mmol) and the pH was adjusted to 8-9 with aq. ammonia and extracted with DCM (3 Å~20 mL/mmol). The combined organic phase was washed with aq. Na$_2$S$_2$O$_3$ (2 Å~10 mL/mmol) and brine (2 Å~10 mL/mmol) then dried over MgSO$_4$, filtered and concentrated. The crude product was purified by flash chromatography (DCM:MeOH, 0-10%) to give the compound 8 (302 mg, 73% yield). APCI MS, m/z 433 [M+H]$_+$, HPLCMS (220 nm)>99% (AUC).

Step 3: (6aR,9R)-5-cyclopropyl-N—((S)-1-hydroxybutan-2-yl)-4,7-dimethyl-4,6,6a,7,8,9-hexahydroindolo[4,3-fg]quinoline-9-carboxamide (Compound D13)

A mixture of 1,2-dimethoxyethane (6 mL/mmol) and water (1.5 mL/mmol) was flushed with argon and a mixture of compound 8 (360 mg, 0.83 mmol), cyclopropylboronic acid (1.5 equiv) and K$_3$PO$_4$ (3.7 equiv) were added to it. The mixture was flushed with argon for 10 min and then Pd(dppf)Cl$_2$ (0.01 equiv) was added, and the resulting mixture was stirred at 90° C. overnight. Then the mixture was cooled to room temperature and diluted with EtOAc (2 mL/mmol) and water (2 mL/mmol). The mixture was filtered and then the layers were separated. The organic phase was washed with brine (10 mL/mmol) then dried over MgSO$_4$, filtered and concentrated. The crude product was purified by preparative HPLC to give compound D13 (25 mg, 7.6% yield). APCI MS, m/z 394 [M+H]$_+$, HPLC-MS (220 nm) 92% (AUC). $^1$H-NMR (300 MHz, DMSO-d$_6$): δ 0.56-0.65 (1H, m); 0.76-0.88 (4H, m); 0.95-1.3 (2H, m); 1.26-1.41 (1H, m); 1.46-1.63 (1H, m); 1.85-1.96 (1H, m); 2.49 (3H, s); 2.55-2.65 (1H, m); 2.96-3.08 (3H, m); 3.13-3.23 (1H, m); 3.28-3.37 (1H, m); 3.45 (1H, dd, J$_1$=5.5 Hz, J$_2$=14.9 Hz); 3.53-3.65 (1H, m); 3.74 (3H, s); 4.58 (1H, t, J=5.5 Hz); 6.42 (1H, d, J$_1$=4.3 Hz); 7.00-7.08 (2H, m); 7.13-7.21 (1H, m); 7.84 (1H, d, J=8.4 Hz).

Scheme 6:

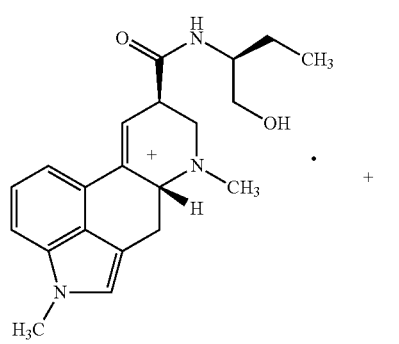

7

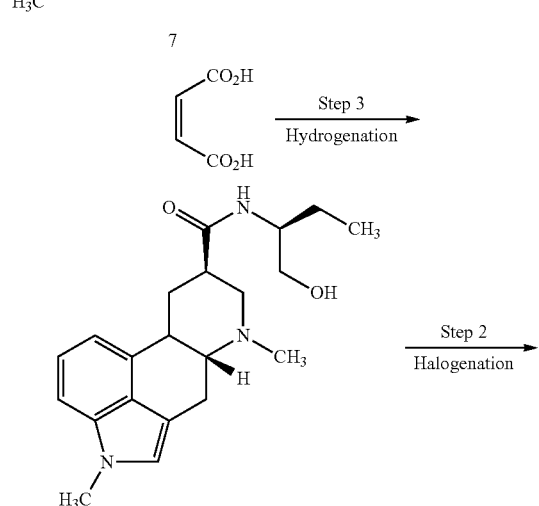

9

-continued

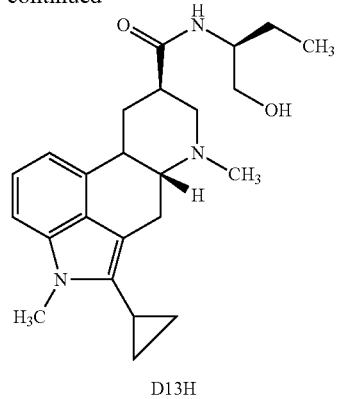

D13H

Example 6: Synthesis of (6aR,9R,10aR)-5-cyclopropyl-N—((S)-1-hydroxybutan-2-yl)-4,7-dimethyl-4,6,6a,7,8,9,10,10a-octahydroindolo[4,3-fg]quinoline-9-carboxamide (Compound 13H)

Step 1: (6aR,9R, 10aR)—N—((S)-1-hydroxybutan-2-yl)-4,7-dimethyl-4,6,6a,7,8,9,10,10a-octahydroindolo[4,3-fg]quinoline-9-carboxamide

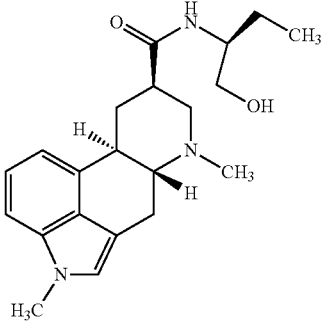

9

Compound 7 (45 mg, 0.1 mmol) was dissolved in MeOH (10 mL/mmol) and Pd/C (0.3 equiv) was added. The reaction mixture was stirred under hydrogen atmosphere (5 bar) in a stainless steel autoclave at room temperature overnight. The reaction mixture was filtered through a pad of Celite™, washed with MeOH (3 Å~5 mL/mmol) and DCM (3 Å~5 mL/mmol), then the filtrate was concentrated. The crude product was purified by flash chromatography (DCM: MeOH, 0-10%) to give compound 9 (29 mg, 85% yield). APCI MS, m/z 356 [M+H]$_+$, HPLCMS (220 nm) 99% (AUC). $^1$H-NMR (300 MHz, DMSO-d$_6$): δ 0.84 (3H, t, J=7.4 Hz); 1.26-1.37 (1H, m); 1.37-1.52 (1H, m); 1.53-1.66 (1H, m); 2.1-2.22 (1H, m); 2.24-2.36 (1H, m); 2.4 (2H, s); 2.43 (2H, s); 2.57-2.89 (3H, m); 2.98-3.08 (1H, m); 3.26-3.32 (2H, m); 3.35-3.42 (2H, m); 3.57-3.69 (1H, m); 3.73 (3H, s); 4.55-4.7 (1H, m); 6.82 (1H, d, J=7.0 Hz); 6.96 (1H, s); 7.08 (1H, t, J=8.0 Hz); 7.18 (1H, d, J=8.0 Hz); 7.64 (1H, d, J=8.4 Hz).

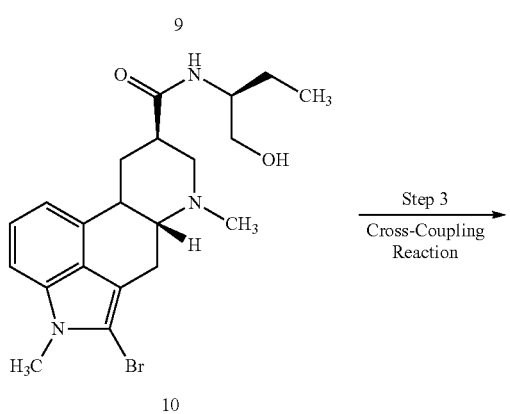

10

Step 2: (6aR,9R, 10aR)-5-bromo-N—((S)-1-hydroxybutan-2-yl)-4,7-dimethyl-4,6,6a,7,8,9,10,10a-octahydroindolo[4,3-fg]quinoline-9-carboxamide

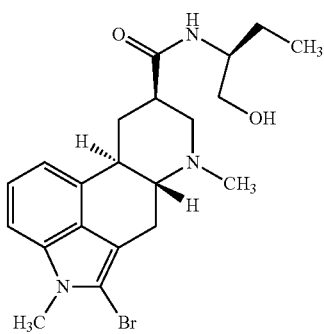

Bromotrimethylsilane (6 equiv) was dissolved in dry DMSO (20 mL/mmol) and the solution was stirred at rt. for 15 min. Compound 9 (380 mg, 1.07 mmol (1 equiv)) was added and the mixture was stirred at room temperature for 10 min. The mixture was poured into ice-water (100 mL/mmol) and the pH was adjusted to 8-9 with aq. ammonia and extracted with DCM (3 Å~20 mL/mmol). The combined organic phase was washed with aq. $Na_2S_2O_3$ (2 Å~10 mL/mmol) and brine (2 Å~10 mL/mmol) then dried over $MgSO_4$, filtered and concentrated. The crude product was purified by flash chromatography (DCM:MeOH, 0-10%) to give the compound 10 (388 mg, 84% yield). APCI MS, m/z 435 $[M+H]_+$, HPLC-MS (220 nm) 98% (AUC).

Step 3: (6aR,9R,10aR)-5-cyclopropyl-N—((S)-1-hydroxybutan-2-yl)-4,7-dimethyl-4,6,6a,7,8,9,10,10a-octahydroindolo[4,3-fg]quinoline-9-carboxamide (Compound D13H)

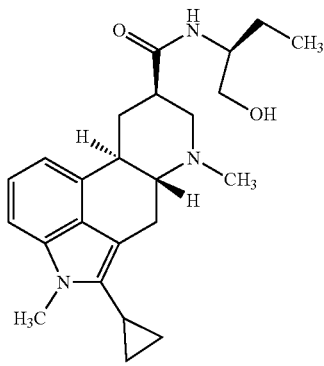

D13H

A mixture of 1,2-dimethoxyethane (6 mL/mmol) and water (1.5 mL/mmol) was flushed with argon and a mixture of compound 10 (385 mg, 0.89 mmol), cyclopropylboronic acid (1.5 equiv) and $K_3PO_4$ (3.7 equiv) were added to it. The mixture was flushed with argon for 10 min and then Pd(dppf)$Cl_2$ (0.01 equiv) was added, and the resulting mixture was stirred at 90° C. overnight. Then the mixture was cooled to room temperature and diluted with EtOAc (2 mL/mmol) and water (2 mL/mmol). The mixture was filtered and then the layers were separated. The organic phase was washed with brine (10 mL/mmol) then dried over $MgSO_4$, filtered and concentrated. The crude product was purified by preparative HPLC to give compound D13H (105 mg, 30% yield). APCI MS, m/z 396 $[M+H]_+$, HPLC-MS (220 nm) 99% (AUC). $^1$H-NMR (300 MHz, DMSO-$d_6$): δ 0.49-0.58 (1H, m); 0.84 (4H, t, J=7.6 Hz); 0.93-1.01 (2H, m); 1.25-1.49 (2H, m); 1.51-1.66 (1H, m); 1.82-2.02 (2H, m); 2.13-2.3 (1H, m); 2.37 (3H, s); 2.41-2.47 (1H, m); 2.56-2.78 (3H, m); 2.88-3.02 (1H, m); 3.23-3.29 (1H, m); 3.34-3.43 (1H, m); 3.57-3.69 (1H, m); 3.73 (3H, s); 4.61 (1H, t, J=5.6 Hz); 6.76 (1H, d, J=7.2 Hz); 7.01 (1H, t, J=7.9 Hz); 7.11 (1H, d, J=8.3 Hz); 7.58 (1H, d, J=7.2 Hz).

Example 7: 5-$HT_7$ Receptor Antagonists were Identified

Compounds A8H, A9H, A16H, A17H, and D13H were shown to be antagonists for the Serotonin 5-$HT_7$ receptor. Antagonist and agonist activities were shown using a cAMP HTRF Assay for Gs Coupled Receptors. The assay was prepared as follows: CHO-K1 cells expressing recombinant human and Serotonin 5-$HT_7$ receptors were grown, prior to analysis, in media without antibiotic. The cells were detached by gentle flushing with PBS-EDTA (5 mM EDTA), recovered by centrifugation, and resuspended in assay buffer (KRH: 5 mM KCl, 1.25 mM $MgSO_4$, 124 mM NaCl, 25 mM HEPES, 13.3 mM Glucose, 1.25 mM $KH_2PO_4$, 1.45 mM $CaCl_2$, 0.5 g/l BSA).

To determine agonist activity (96 well), 12 μL of cells were mixed with 12 μL of the test compound at increasing concentrations and then incubated 30 min at room temperature. After addition of the lysis buffer and 1 hour incubation, cAMP concentrations were estimated according to the manufacturer specification. As shown below in Tables 1a & 1b, no compounds displayed any agonist activity for the Serotonin 5-$HT_7$ receptor.

Antagonist activity was determined in 96 well plates: 12 μL of cells were mixed with 6 μL of the test compound at increasing concentrations and then incubated 10 min. Thereafter 6 μL of the reference agonist was added at a final concentration corresponding to the historical $EC_{80}$. The plates were then incubated for 30 min at room temperature. After addition of the lysis buffer and 1 hour incubation, cAMP concentrations were estimated according to the manufacturer specification. $IC_{50}$ values were used to determine whether a compound acted as an antagonist. Referring to Tables 1a & 1b, Compounds A8H, A9H, A16H, A17H, and D13H each had an $IC_{50}$ value of less than 1 μM for the Serotonin 5-$HT_7$ receptor. Accordingly, these compounds were shown to be antagonists for the Serotonin 5-$HT_7$ receptor.

Example 8: Dopamine $D_{2L}$, $D_3$, Serotonin 5-$HT_{1A}$, 5-$HT_{1B}$, 5-$HT_{1D}$, and 5-$HT_{1F}$ Receptor Agonists and Antagonists Compounds A8H, A9H, A16H, A17H, D13 and D13H were shown to be antagonists and/or agonists of one or more the Dopamine $D_{2L}$, $D_3$, Serotonin, 5-$HT_{1A}$, 5-$HT_{1B}$, 5-$HT_{1D}$, and 5-$HT_{1F}$ Receptors. Antagonist and agonist activities were determined using a GTPγS Scintillation Proximity Assay. The assay was prepared as follows: Membrane extracts were prepared from recombinant human Dopamine $D_{2L}$, $D_3$; Serotonin 5-$HT_{1A}$, 5-$HT_{1B}$, 5-$HT_{1D}$ and 5-$HT_{1F}$ receptors.

Samples were tested by proprietary biological assays by Ogeda S. A., Euroscreen FAST Business Unit, Rue Adrienne Bolland, 47 B-6041 Gosselies, Belgium. Each protein assay was prepared using the following conditions.

5-HT$_{1A}$
- Assay buffer: 20 mM HEPES pH 7.4; 100 mM NaCl, 10 μg/ml saponin, 3 mM MgCl$_2$, 0.1% protease-free BSA;
- Membranes: recombinant 5-HT$_{1A}$ membrane extracts thawed on ice and diluted in assay buffer to give 1 mg/ml (10 μg/well) and kept on ice;
- GDP: diluted in assay buffer to give a 3 μM final assay concentration;
- Beads: PVT-WGA (Perkin Elmer, RPNQ001), diluted in assay buffer at 50 mg/ml (0.5 mg/well); and
- GTPγ[$^{35}$S]: (PerkinElmer NEG030X), diluted in assay buffer to give 0.1 nM;

5-HT$_{1B}$
- Assay buffer: 20 mM HEPES pH 7.4; 100 mM NaCl, 10 μg/ml saponin, 3 mM MgCl$_2$;
- Membranes: recombinant 5-HT$_{1B}$ membrane extracts thawed on ice and diluted in assay buffer to give 1 mg/ml (10 μg/well) and kept on ice;
- GDP: diluted in assay buffer to give a 3 μM final assay concentration;
- Beads: PVT-WGA (Perkin Elmer, RPNQ001), diluted in assay buffer at 50 mg/ml (0.5 mg/well); and
- GTPγ[$^{35}$S]: (PerkinElmer NEG030X), diluted in assay buffer to give 0.1 nM.

5-HT$_{1D}$
- Assay buffer: 20 mM HEPES pH 7.4; 200 mM NaCl, 10 μg/ml saponin, 3 mM MgCl$_2$;
- Membranes: recombinant 5-HT$_{1D}$ membrane extracts thawed on ice and diluted in assay buffer to give 500 mg/ml (5 mg/10 μl) and kept on ice;
- GDP: diluted in assay buffer to give a 30 μM working solution (3 μM final concentration);
- Beads: PVT-WGA (Perkin Elmer, RPNQ001), diluted in assay buffer at 50 mg/ml (0.5 mg/10 μl); and
- GTPγ[$^{35}$S]: (PerkinElmer NEG030X), diluted in assay buffer to give 0.1 nM.

5-HT$_{1F}$
- Assay buffer: 20 mM HEPES pH 7.4; 100 mM NaCl, 10 μg/ml saponin, 1 mM MgCl$_2$;
- Membranes: recombinant 5-HT$_{1F}$ membrane extracts thawed on ice and diluted in assay buffer to give 0.5 mg/ml (5 μg/well) and kept on ice;
- GDP: diluted in assay buffer to give a 3 μM final assay concentration;
- Beads: PVT-WGA (Perkin Elmer, RPNQ001), diluted in assay buffer at 50 mg/ml (0.5 mg/well); and
- GTPγ[$^{35}$S]: (PerkinElmer NEG030X), diluted in assay buffer to give 0.1 nM.

D$_{2L}$
- Assay buffer: 20 mM HEPES pH 7.4; 100 mM NaCl, 10 μg/ml saponin, 30 mM MgCl$_2$, 0.1% protease-free BSA;
- Membranes: recombinant D$_{2L}$ membrane extracts thawed on ice and diluted in assay buffer to give 1 mg/ml (10 μg/well) and kept on ice;
- GDP: diluted in assay buffer to give a 3 μM final assay concentration;
- Beads: PVT-WGA (Perkin Elmer, RPNQ001), diluted in assay buffer at 25 mg/ml (0.25 mg/well); and
- GTPγ[$^{35}$S]: (PerkinElmer NEG030X), diluted in assay buffer to give 0.1 nM.

D$_3$
- Assay buffer: 20 mM HEPES pH 7.4; 100 mM NaCl, 10 μg/ml saponin, 1 mM MgCl$_2$, 0.1% protease-free BSA;
- Membranes: recombinant D$_3$ membrane extracts thawed on ice and diluted in assay buffer to give 1 mg/ml (10 μg/well) and kept on ice;
- GDP: diluted in assay buffer to give a 1 μM final assay concentration;
- Beads: PVT-WGA (Perkin Elmer, RPNQ001), diluted in assay buffer at 50 mg/ml (0.5 mg/well); and
- GTPγ[$^{35}$S]: (PerkinElmer NEG030X), diluted in assay buffer to give 0.1 nM.

Membranes were mixed with GDP (volume:volume 1:1) and incubated for at least 15 min on ice. In parallel, GTPγ[$^{35}$S] is mixed with the beads (volume:volume 1:1) just before starting the reaction.

To determine agonist activity, the following reagents were added in the wells of an Optiplate (Perkin Elmer): 50 μL of test or reference ligand, 10 μL of assay buffer, 20 μl of the membranes:GDP mix, and 20 μL of the GTPγ[$^{35}$S]:beads mix. EC$_{50}$ values were used to determine whether a compound acted as an agonist. Referring to Tables 1a & 1b, EC$_{50}$ values for Compounds A8H, A9H, A17H, D13 and D13H were provided as follows:

- Compound A8H had an EC$_{50}$ value of less than 1 μM for the Dopamine D$_{2L}$ receptor and the Serotonin 5-HT$_{1A}$ receptor;
- Compound A9H had an EC$_{50}$ value of less than 1 μM for the Dopamine D$_{2L}$ receptor;
- Compound A17H had an EC$_{50}$ value of less than 1 μM for the Dopamine D$_3$ receptor;
- Compound D13 had an EC$_{50}$ value of less than 1 μM for the Serotonin 5-HT$_{1D}$ receptor; and
- Compound D13H had an EC$_{50}$ value of less than 1 μM for the Dopamine D$_{2L}$ & D$_3$ receptor and Serotonin 5-HT$_{1B}$, 5-HT$_{1D}$, and 5HT$_{1F}$ receptors.

Accordingly, these compounds were shown to be agonists for one or more of the following: Dopamine D$_{2L}$, D$_3$, Serotonin 5-HT$_{1A}$, 5-HT$_{1B}$, 5-HT$_{1D}$, and 5-HT$_{1F}$ Receptors.

To determine antagonist activity, the following reagents were added in the wells of an Optiplate (Perkin Elmer): 50 μL of test or reference ligand, 20 μL of the membranes:GDP mix, then the plate is incubated 15 minutes at room temperature. After incubation, 10 μL of reference agonist at historical EC$_{80}$ (final concentration) was added, followed by 20 μL of the GTPγ[$^{35}$S]:beads mix.

The plates were covered with a top seal, mixed on an orbital shaker for 2 min, and then incubated for 1 hour at room temperature. Then the plates were centrifuged for 10 min at 2000 rpm, incubated at room temperature 1 hour and counted for 1 min/well with a PerkinElmer TopCount reader. IC$_{50}$ values were used to determine whether a compound acted as an antagonist. Referring to Tables 1a & 1b, IC$_{50}$ values for Compounds A8H, A9H, A16H, A17H, and D13H were provided as follows:

- Compound A8H had an IC$_{50}$ value of less than 1 μM for the Dopamine D$_{2L}$ & D$_3$ receptors and Serotonin 5-HT$_{1A}$, 5-HT$_{1B}$, and 5-HT$_{1D}$ receptors;
- Compounds A9H and A16H had IC$_{50}$ values of less than 1 μM for the Dopamine D$_{2L}$ & D$_3$ receptors and Serotonin 5-HT$_{1B}$/5HT$_{1D}$ receptors;
- Compound A17H had an IC$_{50}$ value of less than 1 μM for the Dopamine D$_{2L}$ & D$_3$ receptors and Serotonin 5-HT$_{1A}$/5HT$_{1D}$ receptors; and
- Compound D13H had an IC$_{50}$ value of less than 1 μM for the Dopamine D$_3$ receptor.

Accordingly, these compounds were shown to be antagonists for one or more of the following: Dopamine $D_{2L}$ & $D_3$ receptors and Serotonin 5-$HT_{1A}$, 5-$HT_{1B}$, and 5-$H_{1D}$ receptors.

Example 9: Adrenergic $\alpha_{1A}$ Receptor and Serotonin 5-$HT_{2A}$, 5-$HT_{2B}$ Agonists and Antagonists Compounds A8H, A9H, A16H, A17H, D13 and D13H were shown to be antagonists and/or agonists of one or more Adrenergic $\alpha_{1A}$ receptor and Serotonin 5-$HT_{2A}$, 5-$HT_{2B}$ Receptors. Antagonist and agonist activities were determined using an IPOne cAMP HTRF assay. The assay was prepared as follows: CHO-K1 cells expressing human recombinant Adrenergic $\alpha_{1A}$, Serotonin 5-$HT_{2A}$, and 5-$HT_{2B}$ receptors grown to mid-log phase in culture media without antibiotics were detached with PBS-EDTA, centrifuged and resuspended in medium without antibiotics buffer. 20,000 cells were distributed in a 96 well plate and incubated overnight at 37° C. with 5% $CO_2$.

To analyze agonist activity, the medium was removed and 20 µl of assay buffer plus 20 µl of test compound or reference agonist were added in each well. The plate was incubated for 60 min. at 37° C. with 5% $CO_2$. $EC_{50}$ values were used to determine whether a compound acted as an agonist. Referring to Tables 1a & 1b, $EC_{50}$ values for Compounds A8H and A9H were provided as follows:

Compound A8H had an $EC_{50}$ value of less than 1 µM for the Serotonin 5-$HT_{2A}$ and 5-$HT_{2B}$ receptors; and Compound A9H had an $EC_{50}$ value of less than 1 µM for the Serotonin 5-$HT_{2A}$ receptor.

Accordingly, these compounds were shown to be agonists for one or more of the following: Serotonin 5-$HT_{2A}$ and 5-$HT_{2B}$ receptors.

To analyze antagonist activity, 20 µl of test compound or reference antagonist was added and the plate is incubated for 15 min. at 37° C. in a humidified atmosphere of 95% air with 5% $CO_2$, then 20 µl of reference agonist at a final concentration corresponding to the historical $EC_{80}$ is added. The plate is incubated for 60 min. at 37° C. with 5% $CO_2$. IP1-D2 reagent and anti-IP1 cryptate reagents are then dispensed in the wells and IP1 concentrations are then measured following the manufacturer recommendations. $IC_{50}$ values were used to determine whether a compound acted as an antagonist. Referring to Tables 1a & 1b, $IC_{50}$ values for Compounds A8H, A9H, A16H, A17H, and D13H were provided as follows:

Compound A8H had an $IC_{50}$ value of less than 1 µM for the Adrenergic $\alpha_{1A}$ receptor and Serotonin 5-$HT_{2A}$ receptor;

Compounds A9H, A16H, and A17H had $IC_{50}$ values of less than 1 µM for the Adrenergic $\alpha_{1A}$ receptor and Serotonin 5-$HT_{2A}$ and 5-$HT_{2B}$ receptors; and Compounds D13 and D13H had $IC_{50}$ values of less than 1 µM for the Serotonin 5-$HT_{2A}$ and 5-$HT_{2B}$ receptors.

Accordingly, these compounds were shown to be agonists for one or more of the following: Adrenergic $\alpha_{1A}$, Serotonin 5-$HT_{2A}$, and 5-$HT_{2B}$ receptors.

Table 1a and 1b, below, displays the agonist ($EC_{50}$) and antagonist ($IC_{50}$) activity of the molecules described above.

TABLE 1a

| | Compound A8H | | Compound A9H | | Compound A16H | |
| --- | --- | --- | --- | --- | --- | --- |
| Receptor | Antagonist Activity (nm) | Agonist Activity (nm) | Antagonist Activity (nm) | Agonist Activity (nm) | Antagonist Activity (nm) | Agonist Activity (nm) |
| $\alpha_{1A}$ | 14 | — | 9.1 | — | 15 | — |
| $D_{2L}$ | 3.5 | 1.1 | 42 | 4.6 | 130 | — |
| $D_3$ | 9.3 | — | 13 | — | 55 | — |
| 5-$HT_{1A}$ | 160 | 31 | — | — | — | — |
| 5-$HT_{1B}$ | 410 | — | 110 | — | 340 | — |
| 5-$HT_{1D}$ | 8 | — | 10 | — | 14 | — |
| 5-$HT_{1F}$ | — | — | — | — | — | — |
| 5-$HT_{2A}$ | 14 | 6.9 | 110 | 12 | 16 | — |
| 5-$HT_{2B}$ | 52 | — | 23 | — | 16 | — |
| 5-$HT_7$ | 110 | — | 190 | — | 380 | — |

TABLE 1b

| | Compound A17H | | Compound D13 | | Compound D13H | |
| --- | --- | --- | --- | --- | --- | --- |
| Receptor | Antagonist Activity (nm) | Agonist Activity (nm) | Antagonist Activity (nm) | Agonist Activity (nm) | Antagonist Activity (nm) | Agonist Activity (nm) |
| $\alpha_{1A}$ | 13 | — | — | — | — | — |
| $D_{2L}$ | 4.2 | 1.1 | — | — | — | 170 |
| $D_3$ | 11 | 8.2 | — | — | 400 | 48 |
| 5-$HT_{1A}$ | 590 | — | — | — | — | — |
| 5-$HT_{1B}$ | — | — | — | — | — | 430 |
| 5-$HT_{1D}$ | 50 | — | — | 730 | — | 11 |
| 5-$HT_{1F}$ | — | — | — | — | — | 260 |
| 5-$HT_{2A}$ | 11 | — | 240 | — | 74 | — |
| 5-$HT_{2B}$ | 25 | — | 140 | — | 3.4 | — |
| 5-$HT_7$ | 140 | — | — | — | 780 | 40 |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

What is claimed is:

1. A method of treating fibrosis or pulmonary arterial hypertension comprising, administering to a subject in need thereof a therapeutically effective amount of a compound represented by structural Formula (I):

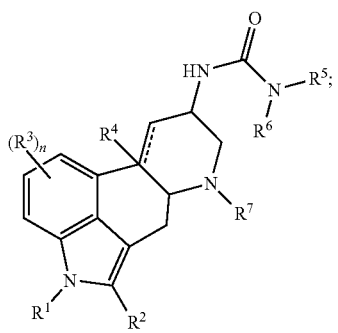

(I)

or a salt thereof, wherein:
- ------ represents an optional double bond;
- $R^1$ is selected from hydrogen; and $C_1$-$C_3$ alkyl, $C_3$-$C_5$ cycloalkyl, $C_{2-4}$ alkenyl, $C_3$-$C_5$ cycloalkenyl, $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)OR^{10}$, —$OC(O)R^{10}$, —$NO_2$, =O, =S, =$N(R^{10})$, and —CN;
- $R^2$ is selected from $C_1$-$C_3$ haloalkyl and $C_3$-$C_5$ cycloalkyl, wherein $C_3$-$C_5$ cycloalkyl is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;
- $R^3$ is selected from halogen, $C_1$-$C_3$ alkyl, $C_1$-$C_3$ haloalkyl, —$OR^{10}$, —$SR^{10}$, —$N(R^{10})_2$, —$C(O)R^{10}$, —$C(O)OR^{10}$, —$OC(O)R^{10}$, —$NO_2$, and —CN;
- $R^4$ is absent or selected from hydrogen and $OR^{10}$, wherein $R^4$ is absent when ------ is a double bond and $R^4$ is selected from hydrogen and $OR^{10}$ when ------ is a single bond;
- $R^5$ is selected from $C_1$-$C_3$ alkyl optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN, wherein when $R^2$ is selected from $C_1$ haloalkyl and ------ is a double bond, $R^5$ is $C_1$-$C_3$ alkyl optionally substituted with one or more substituents independently selected from —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;
- $R^6$ is $CH_2CF_3$;
- $R^7$ is selected from $C_1$-$C_3$ alkyl, $C_{2-4}$ alkenyl, and $C_{2-4}$ alkynyl, each of which is optionally substituted with one or more substituents independently selected from halogen, —$OR^{10}$, —$SR^{10}$, —$C(O)N(R^{10})_2$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, and —CN;
- $R^{10}$ is independently selected at each occurrence from hydrogen; and $C_1$-$C_3$ alkyl optionally substituted with one or more substituents independently selected from halogen, —OH, —$OCH_3$, —$CF_3$, —SH, —$NH_2$, —$NO_2$, and —CN; and
- n is selected from 0, 1, 2, and 3.

2. The method of claim 1, wherein $R^2$ is selected from $C_1$-$C_3$ haloalkyl.

3. The method of claim 2, wherein $R^2$ is $CF_3$.

4. The method of claim 1, wherein $R^2$ is selected from optionally substituted cyclopropyl.

5. The method of claim 1, wherein n is 0.

6. The method of claim 1, wherein $R^4$ is hydrogen.

7. The method of claim 1, wherein $R^5$ is unsubstituted $C_1$-$C_3$ alkyl.

8. The method of claim 7, wherein $R^5$ is methyl, ethyl or propyl.

9. The method of claim 8, wherein $R^5$ is ethyl.

10. The method of claim 1, wherein $R^7$ is methyl.

11. The method of claim 1, represented by:

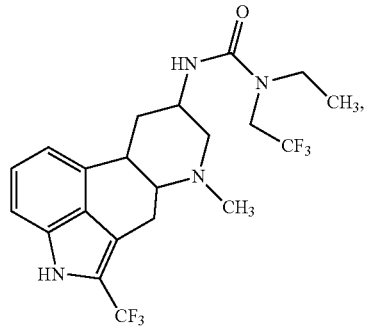

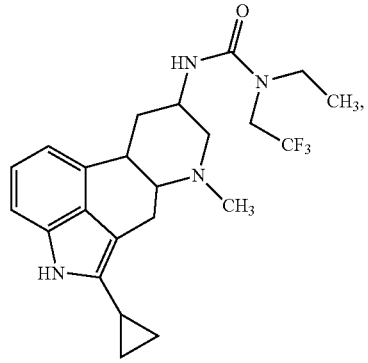

or a salt of any one thereof.

12. The method of claim 1, wherein the method is for treating pulmonary arterial hypertension.

13. The method of claim 1, wherein the method is for treating fibrosis.

14. The method of claim 12, wherein the compound is selected from

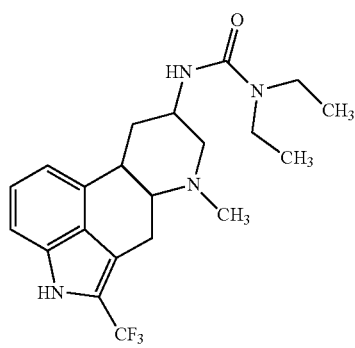 [SMILES: CCN(CC)C(=O)NC1CC2c3cccc4[nH]c(C(F)(F)F)c(c34)CC2N(C)C1]
or a salt of thereof.
15. The method of claim 13, wherein the compound is selected from
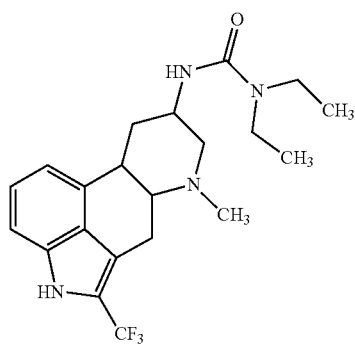 [SMILES: CCN(CC)C(=O)NC1CC2c3cccc4[nH]c(C(F)(F)F)c(c34)CC2N(C)C1]
or a salt thereof.
16. The method of claim 12, wherein the compound is selected from
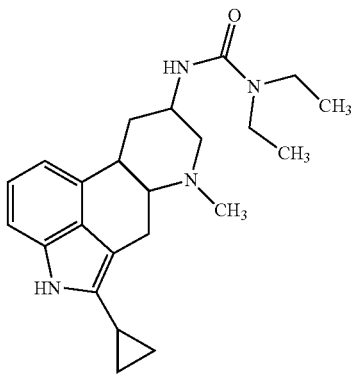 [SMILES: CCN(CC)C(=O)NC1CC2c3cccc4[nH]c(C5CC5)c(c34)CC2N(C)C1]
or a salt thereof.
17. The method of claim 13, wherein the compound is selected from
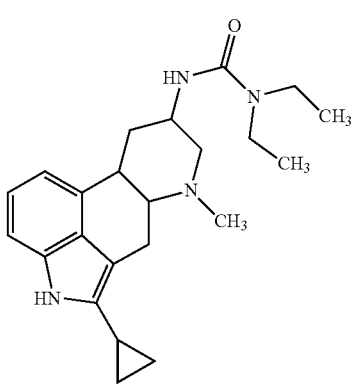 [SMILES: CCN(CC)C(=O)NC1CC2c3cccc4[nH]c(C5CC5)c(c34)CC2N(C)C1]
or a salt thereof.
* * * * *